(12) United States Patent
Niedzwiecki et al.

(10) Patent No.: US 11,419,847 B2
(45) Date of Patent: Aug. 23, 2022

(54) PHARMACEUTICAL MICRONUTRIENT COMPOSITION AND ITS USE TO SIMULTANEOUSLY INHIBIT MULTIPLE CELLULAR MECHANISMS OF INFECTIVITY CAUSED BY CORONAVIRUS, ITS VARIANTS AND MUTANTS

(71) Applicant: Matthias W Rath, Aptos, CA (US)

(72) Inventors: Aleksandra Niedzwiecki, Aptos, CA (US); Matthias W Rath, Aptos, CA (US); Vadim O Ivanov, Castro Valley, CA (US); Anna Goc, Sanjose, CA (US)

(73) Assignee: Matthias W. Rath, Henderson, NV (US)

( * ) Notice: Subject to any disclaimer, the term of this patent is extended or adjusted under 35 U.S.C. 154(b) by 0 days.

(21) Appl. No.: 17/212,727

(22) Filed: Mar. 25, 2021

(65) Prior Publication Data
US 2021/0315857 A1 Oct. 14, 2021

Related U.S. Application Data

(60) Provisional application No. 63/149,633, filed on Feb. 15, 2021, provisional application No. 63/008,560, filed on Apr. 10, 2020, provisional application No. 63/149,636, filed on Feb. 15, 2021, provisional application No. 63/042,821, filed on Jun. 23, 2020, provisional application No. 63/065,564, filed on Aug. 14, 2020.

(51) Int. Cl.

| | |
|---|---|
| *A61K 31/375* | (2006.01) |
| *A61K 31/352* | (2006.01) |
| *A61K 31/198* | (2006.01) |
| *A61K 45/06* | (2006.01) |
| *A61K 36/31* | (2006.01) |
| *A61K 31/12* | (2006.01) |
| *A61K 31/7048* | (2006.01) |
| *A61K 31/05* | (2006.01) |

(52) U.S. Cl.
CPC ............ *A61K 31/352* (2013.01); *A61K 31/05* (2013.01); *A61K 31/12* (2013.01); *A61K 31/198* (2013.01); *A61K 31/375* (2013.01); *A61K 31/7048* (2013.01); *A61K 36/31* (2013.01); *A61K 45/06* (2013.01)

(58) Field of Classification Search
CPC ...... A01N 43/16; A01N 25/004; A01N 35/06; A01N 43/18; A01N 37/20; A01N 43/08; A01N 43/10; A01N 43/32; A01N 43/40; A01N 43/56; A01N 43/60; A01N 43/80
USPC .................................................. 514/456, 466
See application file for complete search history.

(56) References Cited

U.S. PATENT DOCUMENTS

| | | | |
|---|---|---|---|
| 9,192,661 B2 * | 11/2015 | Jain ..................... | A61P 31/14 |
| 9,597,380 B2 * | 3/2017 | Chakraborty .......... | C12N 15/67 |
| 2006/0216251 A1 * | 9/2006 | Morariu ................. | A61K 8/606 |
| | | | 424/769 |
| 2011/0200721 A1 * | 8/2011 | Funda ..................... | A23P 10/30 |
| | | | 426/655 |
| 2013/0196934 A1 * | 8/2013 | Addis .................... | A61K 31/70 |
| | | | 514/23 |

OTHER PUBLICATIONS

PCT search Report, dated Jun. 4, 2021. (Submitted on Sep. 27, 2021).

* cited by examiner

*Primary Examiner* — Sabiha N Qazi

(74) *Attorney, Agent, or Firm* — Geeta Kadambi; Riddhi IP LLC

(57) ABSTRACT

Pharmaceutical micronutrient composition including mixture D in this study helps to mitigate, inhibit, prevent and stop diseases caused by viral infections. The middle east respiratory syndrome-related coronavirus and severe acute respiratory syndrome-related coronavirus as well as their variants and mutants affecting mammals and causing infection are successfully treated using mixture D. Mixture D contains key micronutrients such as an ascorbate, N-acetylcysteine, theaflavins, resveratrol, cruciferous plant extracts, curcumin, quercetin, naringenin, and baicalin and a combination thereof. Additional micronutrients were tested with Mixture D and seemed to have beneficial effects.

14 Claims, 18 Drawing Sheets

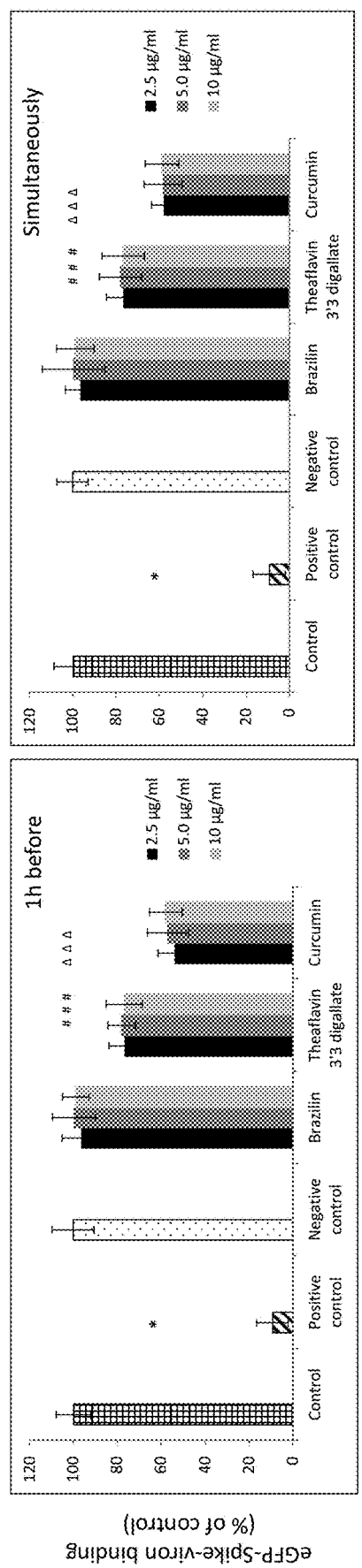
Figure 5A
Figure 5B
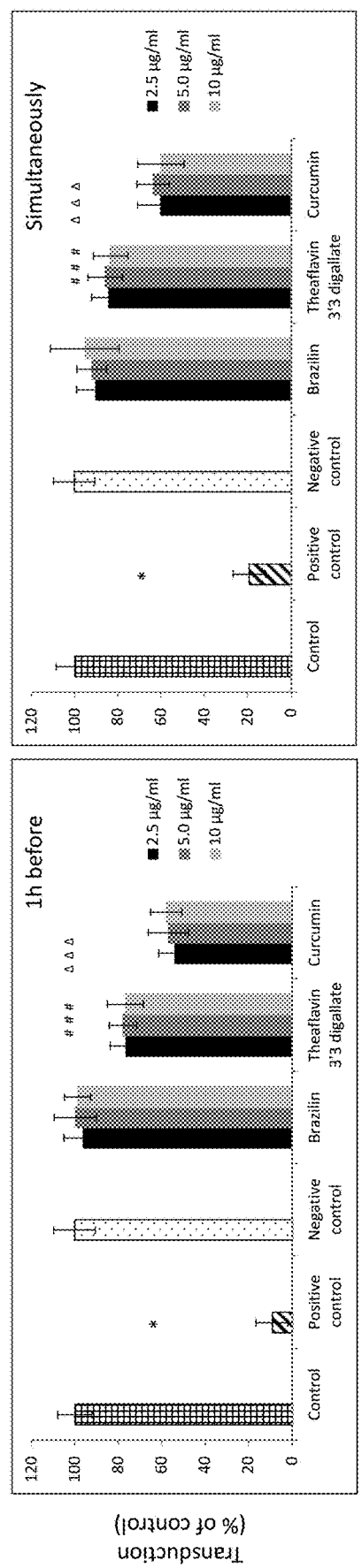
Figure 6A
Figure 6B

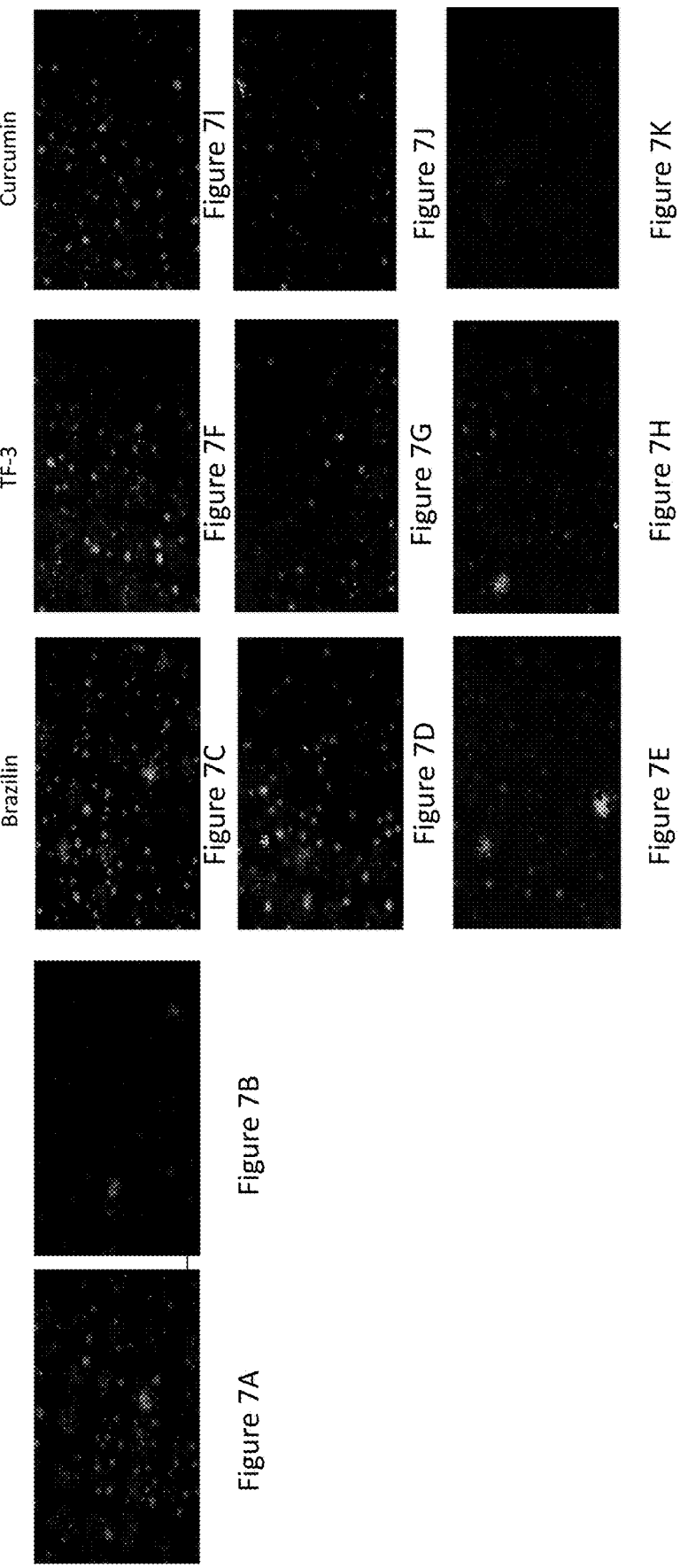

Figure 13

PHARMACEUTICAL MICRONUTRIENT COMPOSITION AND ITS USE TO SIMULTANEOUSLY INHIBIT MULTIPLE CELLULAR MECHANISMS OF INFECTIVITY CAUSED BY CORONAVIRUS, ITS VARIANTS AND MUTANTS

CROSS REFERENCE TO RELATED APPLICATION

The current application claims priority to U.S. provisional application 63/149,633 filed on 15 Feb. 2021, 63/149,636 filed on Feb. 15, 2021, 63/008,560 filed on Apr. 10, 2020, 63/042,821 filed on Jun. 23, 2020, 63/065,564 filed on Aug. 14, 2020. The said US provisional applications are hereby incorporated by reference in its entireties for all of its teachings.

FIELD OF STUDY

This application discloses pharmaceutical micronutrient composition and shows that the said composition simultaneously inhibits multiple cellular mechanisms of infectivity caused by coronavirus and its variants and mitigates coronavirus infection in mammals.

BACKGROUND

The emergence and rapid spread of the coronavirus pandemic has resulted in millions of deaths and is compromising human health and economies on a global scale. Sequencing the whole genome of the virus from patient samples from Wuhan, China (Zhu et al., 2020) identified a new coronavirus that was named severe acute respiratory syndrome coronavirus-2 (SARS-CoV-2) by the Coronavirus Study Group (CSG) of the International Committee on Taxonomy of Viruses (Gorbalenya et al., 2020). The disease caused by the virus was named coronavirus disease 2019 (COVID-19) by the World Health Organization (WHO).

The coronavirus is a rapidly mutating virus and, within one year of the pandemic, several mutations of this virus have emerged in United Kingdom, South Africa, Brazil and other countries, with each of these mutations potentially giving rise to further coronavirus subtypes. Clinical reports show that the British mutation of the coronavirus can infect patients who have received the vaccine developed against the original coronavirus SARS-CoV-2, thereby challenging any claim of a universal efficacy of the available vaccines against all coronavirus mutations.

Thus, it is foreseeable that the ultimate control of the ongoing pandemic caused by the rapidly mutating coronavirus gill be compromised by the need to develop new vaccines potentially for every new coronavirus mutation, and by the related scientific, economic and social consequences of such a strategy.

A promising scientific avenue towards this goal is to focus on the "docking structure" of the coronavirus on the surface of cells, the angiotensin-converting-enzyme 2 (ACE 2) receptor. Significantly, all known coronaviruses, including SARS CoV-2 and its mutations, use this very same receptor as docking structure and entry port for infections. This fact makes a detailed understanding of the regulation of the production expression of this receptor on the surface of human cells—as well related cellular mechanisms a prime target towards developing global health strategies to control the pandemic characterized by a multitude of current and future viral mutations.

The cell entry mechanisms of coronaviruses, including BARS-CoV-2, have been extensively studied. To enter host cells, coronaviruses first bind to a cell surface receptor for viral attachment, subsequently enter cell endosomes, and eventually fuse viral and lysosomal membranes (Li et al., 2016). Coronavirus entry is mediated by a spike protein anchored on the surface of the virus. On mature viruses, the spike protein is present as a trimer, with three receptor-binding S1 heads sitting on top of a trimeric membrane fusion S2 stalk.

The spike S1 protein on SARS-CoV-2 contains a receptor-binding domain (RED) that specifically recognizes its cellular receptor, angiotensin-converting enzyme 2 (ACE2). As such, the receptor-binding domain on SARS-CoV-2 spike protein part S1 head binds to a target cell using the human ACE2 (hACE2) receptor on the cell surface and is proteolytically activated by human proteases. Coronavirus entry into host cells is an important determinant of viral infectivity and pathogenesis (Du et al, 2009, Du et al. 2017).

The cellular receptor for the virus binding is angiotensin-converting enzyme 2 or ACE2, which is an integral membrane protein present on many cells throughout the human body, with strong expression in the heart, vascular system, gastrointestinal system and kidneys, as well as in type II alveolar cells in the lungs. (Zhu et al., 2019, Li et al., 2003, Hoffman et al., 2005). Cellular infections by the coronavirus, as well as intracellular viral replication, is facilitated by several host enzymatic proteins, including transmembrane protease, serine 2 (TMPRSS2), furin, cathepsins, as well as RNA-dependent RNA polymerase (RdPp) catalyzing viral RNA multiplication.

COVID-19 infections have been associated with a high inflammatory response in the host, termed a "cytokine storm", thrombosis and other patho-mechanisms that can trigger a fateful cascade of clinical events associated with advanced coronavirus infections. In evaluating new approaches to inhibiting coronavirus infectivity, the ability of such new approaches to ameliorate such infection-related complications should be an additional target. Thus, there exists an urgent need for preventive and therapeutic strategies for inhibiting the infective mechanisms of all coronaviruses—irrespective of mutation and/or subtype—thereby offering new avenues towards the global control of the pandemic.

SUMMARY

The instant pharmaceutical micronutrient composition prevents, inhibits, treats and delays attachment, penetration, biosynthesis, maturation and release of a coronavirus SARS-Cov-2 virus in a mammal. In one embodiment, the phytochemicals in combination with other vitamins prevents various steps of infection in a mammal. In one embodiment, various combinations of individual micronutrients are called mixtures. In one embodiment, mixture D, a pharmaceutical micronutrient composition is made up of resveratrol, cruciferous plant extract, curcumin, quercetin, naringenin, baicalein, theaflavin, vitamin C and N-actylcysteine.

In another embodiment, a pharmaceutical micronutrient compound comprises an ascorbate in the range of 10 mg to 200,000 mg, N-acetylcysteine in the range of 2 mg to 30,000 mg, theaflavins in the range 5 mg to 3,000 mg, resveratrol in the range of 10 mg to 5,000 mg, cruciferous plant extracts in the range of 5 mg to 5000 mg (or equivalent amount of its active compound, sulforaphane), curcumin in the range of 5 mg to 10,000 mg, quercetin in the range of 5 mg to 2,000 mg, naringenin in the range of 5 mg to 3,000 mg, and baicalein in the range of 5 mg to 3,000 mg.

In another embodiment, additional micronutrients are added to form a pharmaceutical micronutrient compound such as a phenolic acid, gallic acid, tannic acid, chlorogenic acid and rosmarinic acid; a flavonoid such as fisetin, morin, myricetin, kaempferol, rutin, luteolin, baicalin, scutellarin, naringenin, hesperidin, hesperetin, apigenin, genistein, phloroglucinol, schisandrin, urolithin A, punicalagin, brazilin, hispidulin, papaverine, silymarin, procyanidin B2, procyanidin B3, stilbenes and pterostilbene; an alkaloid such as palmatine, berberine, cannabidiol, castanospermine, usnic acid, malic acid, terpenes, D-limonene and carnosic acid.

In another embodiment, a pharmaceutical micronutrient mixture consists of an ascorbate in the range of 10 mg to 200,000 mg, N-acetylcysteine in the range of 2 mg to 30,000 mg, theaflavins in the range 5 mg to 3,000 mg, resveratrol in the range of 10 mg to 5,000 mg, cruciferous plant extracts in the range of 5 mg to 5,000 mg (or equivalent amount of its active compound, sulforaphane), curcumin in the range of 5 mg to 10,000 mg, quercetin in the range of 5 mg to 2,000 mg, naringenin in the range of 5 mg to 3,000 mg, and baicalein in the range of 5 mg to 3,000 mg. In another embodiments, the ascorbates are at least one of or a combination of L-ascorbic acid, magnesium ascorbate, calcium ascorbate, ascorbyl palmitate, ascorbyl phosphate, sodium ascorbyl phosphate and/or or another pharmaceutically acceptable form of ascorbate.

In another embodiment, the pharmaceutical micronutrient composition further consists of at least one of the theaflavins in the range 5 mg to 3,000 mg, resveratrol in the range of 10 mg to 5,000 mg, cruciferous plant extracts in the range of 5 mg to 5,000 mg, curcumin in the range of 5 mg to 10,000 mg, quercetin in the range of 5 mg to 2,000 mg, and a combination thereof.

In another embodiment, several additional ingredients are added, to form a pharmaceutically acceptable formulation for various forms of use, such as oral, injectable, absorbable, etc. The pharmaceutical micronutrient composition is in the form of oral, non-invasive peroral, topical (for example, transdermal), enteral, transmucosal, targeted delivery, sustained-release delivery, delayed release, pulsed release and parenteral methods.

In one embodiment, wherein the viral infection and/or viral disease uses a cellular receptor for a viral entry on a surface of an epithelial cells, endothelial cells and/or other cell types.

In another embodiment, the viral infection and/or viral disease is that which uses an angiotensin converting enzyme 2 (ACE2) receptor on the surface of an epithelial cell, endothelial cell and other cell types, for the viral entry, is treated, prevented and mitigated using pharmaceutical micronutrient composition.

The pharmaceutical micronutrient composition, in one embodiment, is used to treat the human and other species with severe acute respiratory syndrome-related coronaviruses (SARS-CoV-1, SARS-CoV2 and their variants) that use angiotensin converting enzyme 2 (ACE2) receptors on the surface of epithelial cells, endothelial cells and other cell types, for viral entry.

The pharmaceutical micronutrient composition, in one embodiment, is used to treat the human and other species with Middle East respiratory syndrome-related coronavirus (MERS-CoV), and its variants that use the angiotensin converting enzyme 2 (ACE2) receptors on the surface of epithelial cells, endothelial cells and other cell types, for viral entry. The pharmaceutical micronutrient composition, in one embodiment, is mixture D, which is used in humans to treat, prevent, inhibit and stop inflammation caused by severe acute respiratory syndrome-related coronaviruses (SARS-CoV-1, SARS-CoV-2 and their variants), and Middle East respiratory syndrome-related coronavirus (MERS-CoV) and its variants.

Others features of the present embodiments will be apparent from the accompanying drawings and from the detailed description that follows.

BRIEF DESCRIPTION OF DRAWINGS

Example embodiments are illustrated by way of example and not limitation in the figures of the accompanying drawings, in which like references indicate similar elements and in which:

FIGS. 5A and 5B show SARS-CoV-2 pseudo-virions binding to cells at different patterns of treatment.

FIGS. 6A and 6B show SARS-CoV-2 pseudo-virions entry to cells at different pattern of treatment.

FIGS. 7A, 7B, 7C, 7D, 7E, 7F, 7G, 7H, 7I, 7J, 7K show images of syncytia taken after treatment with indicated polyphenols.

FIG. 13 shows inhibition of cellular entry of the mutated forms of SARS-CoV-2: viral strains from the UK, Brazil, and South Africa, upon application of different patterns of treatment.

DETAILED DESCRIPTION

The life cycle of the virus with the host consists of the following five steps: attachment, penetration, biosynthesis, maturation, and release. Once viruses bind to host receptors (attachment), they enter host cells through endocytosis or membrane fusion (penetration). Once viral contents are released inside the host cells, viral RNA enters the nucleus for replication. Viral messenger RNA (mRNA) is used to make viral proteins (biosynthesis). New viral particles are then made (maturation) and released. Coronaviruses consist of four structural proteins: spike (S), membrane (M), envelope (E) and nucleocapsid (N). Spike is composed of a transmembrane trimetric glycoprotein protruding from the viral surface, which determines the diversity of coronaviruses and host tropism.

Since several mechanisms are involved in the pathogenicity of SARS-CoV-2 all of which are ultimately regulated at the level of cellular metabolism, the most effective approach to viral infectivity suppression is by identifying molecules that are able to safely regulate and/or inhibit the expression of infection-pathway-related proteins.

Figure 1A:
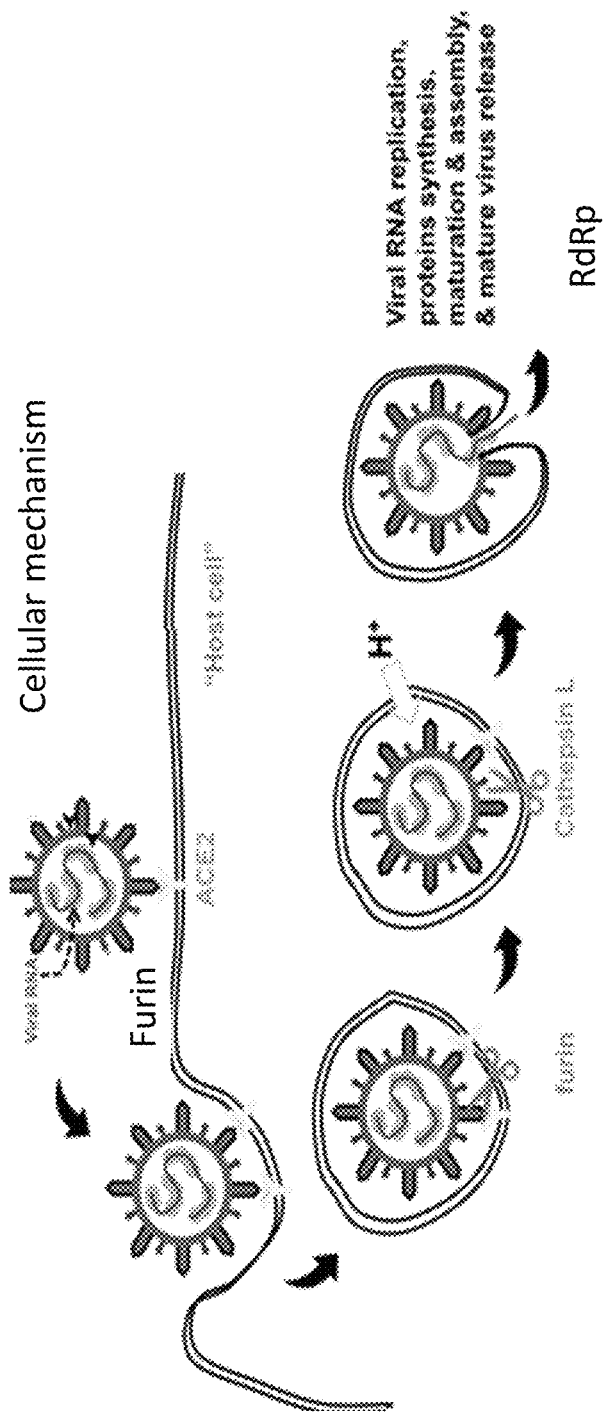
FIGS. 1A and 1B show several cellular and systemic mechanisms of coronavirus infection.
Figure 1B:
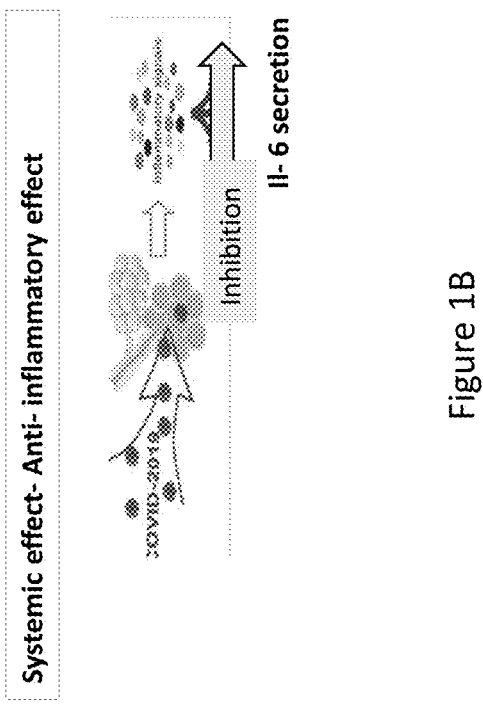

FIG. 1A shows the cellular mechanism of viral entry and several entry points for the SARS-CoV-2 virus and others through ACE2 receptors, which, having entered, require furin and cathepsin L for replication, protein synthesis, maturation and release into the bloodstream. FIG. 1B shows the systemic effect of the release of interleukin 6 (IL-6) in response to inflammation caused by viral infection. IL-6 may be a therapeutic target for inhibiting the cytokine storm and cytokine storm-associated organ damage. We would show that this is a good target to prevent organ damage.

The safest and most effective molecules able to exert such a regulatory role are natural compounds, namely micronutrients. These natural compounds are by their very nature able to affect simultaneously, multiple biochemical processes in cellular metabolism.

A "mammal" to be treated by the subject method may mean either a human or non-human animal, such as mice, primates and vertebrates. The specific diseases that would be targets for a treatment using a pharmaceutical micronutrient composition are infections caused by SARS-CoV-2, SARS-CoV-2 variants (such as the UK, Nigeria, South Africa and Brazil variants, and 19 other mutations), MERS-CoV (the beta coronavirus that causes Middle East respiratory syndrome, or MERS), SARS-CoV (the beta coronavirus that causes severe acute respiratory syndrome, or SARS), SARS-CoV-2, and all their subtypes, four main sub-groupings of coronaviruses, known as alpha, beta, gamma and delta.

Our earlier study showed that a natural micronutrient composition containing vitamin C, certain minerals, amino acids and plant extracts was effective in significantly decreasing cellular ACE2 expression in human lung alveolar epithelial and vascular endothelial cells. Also, a combination of phytobiological compounds demonstrated efficacy in inhibiting viral binding to ACE2 cellular receptors and affecting other mechanisms associated with viral infectivity.

Here we claim the efficacy of certain combinations of micronutrients in significantly inhibiting coronavirus infectivity, including viral binding to the ACE2 receptor, viral entry into the cell, intracellular viral replication, and other mechanisms. In this study we tested the efficacy of a specific nutrient compositions containing vitamin C, N-acetylcysteine, resveratrol, theaflavins, curcumin, quercetin, naringenin, baicalin and extracts of cruciferous plants (broccoli, cabbage, cauliflower) on key aspects of CoV infectivity: inhibition of viral RBD binding to ACE2 receptors, cellular expression of ACE2 receptors, inhibition of key enzymes involved in coronavirus activity, and anti-inflammatory and anti-coagulant effects of this formulation.

The results show that this micronutrient composition was effective in inhibiting RBD binding of spike protein of SARS-CoV-2 to the ACE2 receptor (by about 75% at 5 mcg/ml and 85% inhibition at 10 mcg/ml). At these concentrations, this micronutrient composition should be considered as a safe and affordable approach in controlling the current COVID-19 pandemic. MATERIAL AND METHODS Cell cultures: Human Small Airways Epithelial Cells (HSAEpC, purchased from ATCC) were cultured in Airways Epithelial Cells Growth Medium (ATCC) in plastic flasks at 37° C. and 5% $CO_2$. For the experiment HSAEpC, passage 5-7, were plated to collagen-covered 96-well plastic plates (Corning) in 100 µL growth medium and were grown to confluent layer for 4-7 days. Human cell lung epithelial cell line A549 (obtained from ATCC) was cultured in DMEM supplemented with 10% fecal bovine serum.

Micronutrient composition: the micronutrient combination used in our experiments was developed at the Dr. Rath Research Institute (San Jose, Ca). The composition of all five mixtures tested is presented in Table 1.

TABLE 1

All micronutrients used in different combinations as mixtures:

Micronutrient- Mixture D

Vitamin C
N-acetylcysteine
Theaflavin-3,3'-digallate
Resveratrol
Cruciferous plant extracts
Curcumin
Quercetin
Naringenin
Baicalin

TABLE 2

Mixture A, mixture B, mixture C, mixture D and mixture E are represented in corresponding column A, B, C, D and E.

| Ingredients | A | B | C | D | E |
|---|---|---|---|---|---|
| Green Tea Extract | X | X | X | | |
| Resveratrol | X | X | X | X | X |
| Cruciferex | X | X | X | X | X |
| Curcumin | X | X | X | X | X |
| Quercetin | X | X | X | X | X |
| Naringenin | X | X | X | X | X |
| Baicalin | X | X | X | X | X |
| Theaflavin | X | | | X | X |
| Vitamin C | X | X | X | X | X |
| N-acetylcycteiene | | X | | X | |
| Fucoidan | | X | | | X |

Cell-Cell fusion assay: Cell-cell fusion assay was performed according to Ou et al. Briefly, A549 cells transduced with eGFP-luciferase-SARS-CoV-2 spike S1 lentivirus vector (GenScript, Piscataway, N.J.) were detached with 1 mM EDTA, treated with indicated concentrations of selected polyphenols for 1 h. at 37° C. and overlaid on 80-95% confluent human A549 lung epithelial cells overexpressing hACE2. After 4 h. incubation at 37° C., images of syncytia were captured with a Zeiss Axio Observer A1 fluorescence microscope (Carl Zeiss Meditec, Inc, Dublin, Calif.). Positive control was 20 µm/ml anti-ACE2 antibody. Results are expressed as a percentage of polyphenol-free control (mean+/−SD, n=3).

Cell supplementation: The micronutrient mixture was dissolved in DMSO either as 1 mg/ml or 10 mg/ml stock solutions. For ACE2 expression experiments HSAEpC cells were supplemented with indicated doses of the formulation in 100 µL/well cell growth medium for 3-7 days. Applied nutrient concentrations were expressed as micrograms per ml (ug/ml).

ACE-2 expression assay (ELISA): Human Small Airways Epithelial Cells (HSAEpC) were supplied by ATCC (American Type Culture Collection, Manassas, Va.) and cultured in Small Airways Epithelial Cells culture medium (ATCC). HSAEpC cells were seeded in 96-well plates covered with collagen at 6 passage and grown to confluent layer. Cell culture medium was supplemented with indicated amounts of mixture D and 50 mcg/ml ascorbic acid in 100 mcl per well. After 72 h. cells were supplemented with fresh medium and the same addition for another 72 h. After 6 days' incubation, cell layers were washed twice with phosphate-buffered saline (PBS) and fixed with 3% formaldehyde in PBS with 0.5% Triton X100 for 1 h. at 4° C. Fixed cells were washed four times with PBS and incubated with 1% bovine serum albumin (BSA) in PBS overnight at 4° C. ACE2 expression was measured with ELISA assay using primary anti-ACE2 polyclonal antibodies (SIGMA) and secondary goat anti-mouse IgG antibodies conjugated with horseradish peroxidase (HRP, Rockland). Amounts of retained HRP were determined by HRP substrate colored reaction as optical density at 450 nm using a microplate reader. Results were calculated with Microsoft Excel software and presented as percentage of unsupplemented controls (an average of three repetitions+/−standard deviation).

Receptor binding and entry assays: cell lines and pseudoviruses: Human alveolar epithelial cell line A549 was obtained from ATCC. Human alveolar epithelial cell line A549, stably overexpressing hACE2 receptor (hACE2/A549), was obtained from GenScript (Piscataway, N.J.). Both cell lines were maintained in Dulbecco's MEM containing 10% fetal bovine serum (FBS), 100 U/ml penicillin and 100 µg/ml streptomycin. Pseudovirus particles with spike glycoprotein as the envelope protein, with eGFP and luciferase (eGFP-luciferase-SARS-CoV-2 spike glycoprotein pseudotyped particles) and pseudotyped ΔG-luciferase (G*ΔG-luciferase) rVSV, were purchased from Kerafast (Boston, Mass.). Bald pseudovirus particles with eGFP and luciferase (eGFP-luciferase-SARS-CoV-2 pseudo-typed particles) were purchased from BPS Bioscience (San Diego, Calif.). Lentiviral particles carrying human TMPRSS2 were from Addgene (Watertown, Mass.).

Test compounds, antibodies, recombinant proteins and inhibitors: Curcumin, tea extract standardized to 85% theaflavins, theaflavin-3,3'-digallate, gallic acid, tannic acid, *Andrographis paniculata* extract, andrographolide, licorice extract, glycyrrhizic acid, broccoli extract, L-sulforaphane, usnic acid, malic acid, D-limonene and ammonia chloride were purchased from Sigma (St. Louis, Mo.). All other polyphenols and camostat mesylate were obtained from Cayman Chemical Company (Ann Arbor, Mich.). All antibodies were from Santa Cruz Biotechnology (Santa Cruz, Calif.). TMPRSS2 recombinant protein was from Creative BioMart (Shirley, N.Y.).

SARS-CoV-2 RBD binding to hACE2: Binding/neutralization reaction was performed using a SARS-CoV-2 surrogate virus neutralization test kit that can detect either antibody or inhibitors that block the interaction between the receptor binding domain (RBD) of the SARS-CoV-2 spike protein and the hACE2 cell surface receptor (GenScript, Piscataway, N.J.). For screening assay tested polyphenols at 100 µg/ml were incubated with either HRP-conjugated receptor-binding domain (RBD fragment) of SARS-CoV-2 spike S1 domain, or with hACE2 immobilized on 96-well plate for 30 min. at 37° C. Next, the samples that were incubated with RBD fragment were transferred into 96-well plate with immobilized hACE2 receptor and incubated for additional 15 min. at 37° C., whereas hACE2 immobilized plates already incubated with different polyphenols were washed four times with washing buffer and treated with HRP-conjugated RBD fragments, and then incubated for 15 min. at 37° C. Subsequently, all plates were washed four times with washing buffer and developed with tetramethylbenzidine (TMB) substrate solution for up to 5 min. followed by the addition of stop buffer. Optical density was measured immediately at 450 nm with a plate reader (Molecular Devices, San Jose, Calif.). Positive and negative controls were provided by the manufacturer. Results are expressed as a percentage of polyphenol-free control (mean+/−SD, n=5).

RBD binding: This assay was performed using a GenScript SARS-CoV-2 surrogate virus neutralization test kit that can detect either antibody or inhibitors that block the interaction between the RBD of the viral spike protein with the ACE2 cell surface receptor. All test samples with indicated concentrations, and positive and negative controls (provided by the manufacturer) were diluted with the sample dilution buffer with a volume ratio of 1:9. In separate tubes, HRP-conjugated RBD was also diluted with the HRP dilution buffer with a volume ratio of 1:99. Binding/neutralization reaction was performed according to manufacturer's protocol. Briefly, diluted positive and negative controls as well as the test samples with indicated concentrations were mixed with the diluted HRP-RBD solution with a volume ratio of 1:1 and incubated for 30 min. at 37° C. Next, 100 µL each of the positive control mixture, negative control mixture, and the test sample mixtures were added to the corresponding wells with immobilized ACE2 receptor and incubated for 15 min. at 37° C. Subsequently, the plates were washed four times with 260 µl/well of the 1× wash solution, and TMB solution was added to each well (100 µl/well). Plates were incubated in the dark at room temperature for up to 5 min. Next, 50 µl/well of stop solution was added to quench the reaction, and the absorbance was measured immediately in plate reader at 450 nm. Experiment was performed three times in duplicates. Data are presented as % of control.

Binding of pseudo-typed virion mutants of SARS-CoV-2 to hACE2 receptor: The experiment was conducted according to GenScript recommendations with small modifications. Briefly, eGFP-luciferase-SARS-CoV-2 spike protein encapsulated pseudo-virions were incubated at 37° C. with 5 and 10 µg/ml of mixture D and simultaneously added to hACE2/A549 cells. Cells were incubated for an additional 1 h. at 37° C. Subsequently, cells were washed three times with washing buffer, and primary antibody against SARS-CoV-2 spike protein at 1:1000 dilution, followed by HRP-conjugated secondary antibody at 1:2500 dilution, were employed in ELISA assay. The transduction efficiency was quantified by recording of the luciferase activity, utilizing a luciferase assay system (Promega, Madison, Wis.) and a spectrofluorometer (Tecan Group Ltd., Switzerland). Positive and negative controls were provided by the manufacturer. Data are presented as % of control without mixture addition (mean+/−SD, n=6).

Cathepsin L activity assay: Experiment was performed in cell lysates using a Cathepsin L Activity Assay Kit (Abcam, Cambridge, Mass.) according to the manufacturer's protocol. Briefly, $5 \times 10^6$ A549 cells treated with mixture D at 5 and 10 μg/ml concentrations for 24 h. were washed with cold 1×PBS, and lysed 100 μl with CL buffer for 8 min. After 3 minutes of centrifugion at 4° C., supernatants were collected and enzymatic reaction was set up by mixing 50 μl of treated sample, 50 μl of control sample, 50 μl of background control sample, 50 μl of positive and negative controls. Next, 50 μl CL buffer and 1 μl 1 mM DTT were added, followed by addition of 2 μl of 10 mM CL substrate Ac-FR-AFC, except for the background control. Samples were incubated at 37° C. for 1 h. and fluorescence was recorded at extension/emission=400/505 nm with a fluorescence spectrometer (Tecan Group Ltd., Switzerland). Data are presented as % of control without PB addition (mean+/−SD, n=6).

Effect of mixture D on the activity of isolated cathepsin L was tested using Cathepsin L Activity Screening Assay Kit (BPS Bioscience, San Diego, Calif.) according to the manufacturer's protocol. Briefly, mixture D at 5.0 and 10 μg/ml concentrations was added to cathepsin L (0.2 mU/μl) for 15 mins at 22° C., prior to fluorogenic substrate (Ac-FR-AFC) (10 μM) addition and incubation for 60 mins at RT. Positive control contained only cathepsin L, and negative control containing cathepsin L and cathepsin L inhibitor E64 d (25 μM). The fluorescence was recorded at extension/emission=360/480 nm with a fluorescence spectrometer (Tecan Group Ltd., Switzerland). Data are presented as a percentage of control without PB addition (mean+/−SD, n=6).

Furin activity assay: Effects of mixture D on furin enzymatic activity were evaluated using a SensoLyte Rh110 Furin Activity Assay Kit (AnaSpec, Fremont, Calif.) in accordance with the manufacturer's protocol. Briefly, mixture D at 10 and 20 μg/ml concentrations was mixed with furin recombinant protein for 15 min., followed by the addition of fluorogenic Rh110 furin substrate. The samples were incubated for 1 h. at 22° C. and the fluorescence was recorded at extension/emission=490/520 nm with a fluorescence spectrometer (Perceptive Biosystems Cytofluor 4000). Results were calculated with Microsoft Excel software and presented as a percentage of unsupplemented controls (an average of three repetitions+/−standard deviation).

In vitro RdRp activity: In vitro RdRp activity was examined using a SARS-CoV-2 RNA Polymerase Assay Kit (ProFoldin, Hudson, Mass.) according to the manufacturer's protocol. Briefly, 0.5 μl of 50× recombinant RdRp was incubated with 2.5 μl of 50× buffer and 21 μl of Mixture D at 5 and 10 μg/ml concentrations for 15 min at RT, followed by the addition of master mix containing 0.5 μl of 50×NTPs and 0.5 μl of 50×template (as a single-stranded polyribonucleotide). The reaction (25 μl) was incubated for 2 h at 34° C. and then stopped by addition of 65 μl of 10×fluorescence dye, and the fluorescence signal was recorded within 10 min at extension/emission=488/535 nm using a fluorescence spectrometer (Tecan, Group Ltd., Switzerland). Results are expressed as a percentage of control without PB addition (mean+/−SD, n=6).

Interleukin 6 (IL-6) assay: Human Small Airways Epithelial Cells (HSAEpC) were supplied by ATCC and cultured in Small Airways Epithelial Cells culture medium (ATCC). SAEC cells were seeded in six-well plates covered with collagen at 6 passage and grown to confluent layer. Cell culture medium was supplemented with indicated amounts of Mixture D mixture, 50 mcg/ml ascorbic acid and Vitamin D3 in 3 ml per well. After 72 hours incubation conditioned media were collected and IL-6 content was measured using R&D Systems Human IL6 ELISA assay in accordance with the manufacture's protocol. Results were calculated with Microsoft Excel software and presented as a percentage of unsupplemented controls (an average of three repetitions+/−standard deviation).

RESULTS

Our study helps to unravel previously unidentified but important antiviral mechanisms of natural compounds and expands our understanding of SARS-CoV-2 biology. Clinical evaluation of their efficacy in SARS-CoV-2 pathophysiology would be particularly interesting during later steps of the infection process. This should include their effects on host responses following SARS-CoV-2 infection and whether or not their antiviral potential could support or complement current pharmacological treatments.

Efficacy of polyphenols and plant extracts in preventing binding of the RBD sequence of SARS-CoV-2 and hACE2 receptor. We investigated the ability of several classes of polyphenols to inhibit the binding of the RBD sequence of the SARS-CoV-2 spike protein to the hACE2 receptor taking a two-stage approach. In the first step we screened 51 different polyphenols and plant extracts for their ability to inhibit binding of an HRP-conjugated RBI) fragment of SARS-CoV-2 spike protein to the immobilized hACE2 receptor and its direct binding to the hACE2 receptor itself.

As presented in Table 3 and Table 4, three polyphenols, brazilin, theaflavin-3,3'-digallate, and curcumin, showed the highest efficacy (100%) in inhibiting RBD binding to hACE2 when used at 100 μg/ml concentrations. At the same time these and other tested polyphenols did not significantly bind to the ACE2 receptor itself.

Here, we provide in vitro experimental evidence that among 51 polyphenols selected in this study, brazilin, theaflavin-3,3'-digallate and curcumin exhibited the highest affinity in binding to the RBD-spike protein of SARS-CoV-2. While curcumin, at considerably low concentrations, showed moderate binding to hACE2 receptor, neither brazilin, nor theaflavin-3,3'-digallate displayed binding affinity to this receptor.

We further investigated this effect by using hA549 cells expressing spike protein. By applying spike-protein-enveloped pseudo-virions and a different pattern of exposure to polyphenols, we observed that all three polyphenol compounds can inhibit viral attachment to the cell surface ACE2 receptors after both short-term (1 h. and 3 h.) and long-term (48 h.) exposure or incubation pattern. When the SARS-CoV-2 virions were pre-incubated with these compounds for 1 h, added simultaneously, or when the compounds were added 1 h. post-infection, the virions' ability to bind to cell surface ACE2 receptors and transduce cells was decreased by all test compounds in dose-dependent fashion. Interestingly, the same inhibitory effect of polyphenols, although at their higher but still non-toxic concentrations, was observed when SARS-CoV-2 pseudo-virions where forcibly attached to the cells by spinfection. In addition, we noticed that brazilin, theaflavin-3,3'-digallate, and curcumin can reduce cell-cell fusion between spike-expressing cells and hACE2 overexpressing cellular monolayer. These results collectively indicate that all these three compounds have inhibitory properties directed especially towards RBD-SARS-CoV-2.

TABLE 3

Effects of various classes of polyphenols in preventing RBD of SARS-CoV-2 binding and ACE2 receptor binding.

| Tested polyphenols and alkaloids (0.1 mg/ml) | Binding with RBD (% of control ± SD) | Binging with ACE2 (% of control ± SD) |
|---|---|---|
| Phenolic acids | | |
| Gallic acid | 18.3 ± 4.5 | 6.5 ± 1.3 |
| Tannic acid | 79.4 ± 2.3 | 7.2 ± 2.3 |
| Curcumin | 100 ± 0.2 | 4.6 ± 2.4 |
| Chlorogenic acid | 25.5 ± 2.5 | 4.7 ± 1.6 |
| Rosmarinic acid | 22.5 ± 3.8 | 7.9 ± 1.8 |
| Flavonoids | | |
| Fisetin | 22.4 ± 1.9 | 6.0 ± 2.4 |
| Quercetin | 22.4 ± 6.5 | 7.8 ± 3.3 |
| Morin | 30.5 ± 5.8 | 5.6 ± 3.1 |
| Myricetin | 45.5 ± 5.4 | 5.6 ± 2.1 |
| Kaempferol | 15.6 ± 2.9 | 6.2 ± 2.5 |
| Rutin | 20.6 ± 6.3 | 4.8 ± 2.0 |
| Luteolin | 10.4 ± 4.7 | 4.8 ± 1.6 |
| Baicalein | 22.5 ± 5.1 | 7.4 ± 1.4 |
| Baicalin | 10.3 ± 2.9 | 4.9 ± 1.9 |
| Scutellarin | 8.1 ± 3.7 | 7.5 ± 1.7 |
| Naringin | 23.6 ± 6.4 | 3.7 ± 1.1 |
| Naringenin | 20 ± 5.1 | 8.3 ± 1.6 |
| Hesperidin | 90.3 ± 3.8 | 8.3 ± 2.3 |
| Hesperetin | 42.5 ± 4.6 | 4.9 ± 2.7 |
| Apigenin | 17.1 ± 4.1 | 8.3 ± 1.9 |
| Genistein | 22.1 ± 2.8 | 9.4 ± 2.7 |
| Phloroglucinol | 69.5 ± 3.6 | 5.9 ± 3.4 |
| Schisandrin | 22.4 ± .3.3 | 5.1 ± 2.7 |
| Urolithin A | 31.1 ± 4.6 | 8.8 ± 1.6 |
| Punicalagin | 32.3 ± 5.9 | 5.4 ± 2.3 |
| Brazilin | 100 ± 0.1 | 4.6 ± 2.2 |
| Hispidulin | 20.1 ± 6.0 | 7.4 ± 2.1 |
| Papaverine | 1.6 ± 0.2 | 6.5 ± 3.7 |
| Silymarin | 30.0 ± 2.6 | 8.8 ± 3.8 |
| Procyanidin B2 | 31.1 ± 3.6 | 5.8 ± 2.7 |
| Procyanidin B3 | 32.3 ± 3.7 | 7.8 ± 2.7 |
| Stilbenes | | |
| Trans-resveratrol | 22.3 ± 2.9 | 5.5 ± 2.4 |
| Pterostilbene | 23.1 ± 2.8 | 9.4 ± 2.5 |
| Alkaloids | | |
| Palmatine | 40.4 ± 6.1 | 8.5 ± 2.7 |
| Berberine | 17.3 ± 2.7 | 9.4 ± 2.4 |
| Cannabidiol | 1.4 ± 0.3 | 5.8 ± 2.0 |
| Castanospermine | 8.2 ± 2.3 | 5.5 ± 3.1 |
| Usnic acid | 22.0 ± 3.4 | 5.7 ± 1.7 |
| Malic acid | 1.2 ± 3.7 | 5.8 ± 1.4 |
| Terpenes | | |
| D-limonene | 27.2 ± 6.4 | 6.4 ± 1.5 |
| Carnosic acid | 27.1 ± 5.1 | 6.9 ± 4.1 |

TABLE 4

Binding ability of selected plant extracts and their major components, to RBD of SARS-CoV-2 and to ACE2 receptor.

| Tested plant extracts (0.1 mg/ml) | Binding to RBD (% of control ± DS) | Binging to ACE2 (% of control ± DS) |
|---|---|---|
| Tea extract (85% catechin standardized) | 88.3 ± 3.7 | 5.4 ± 1.2 |
| (+)-gallocatechin | 69.5 ± 2.8 | 5.7 ± 1.6 |
| (−)-catechin gallate | 37.4 ± 4.7 | 8.6 ± 1.5 |
| (−)-gallocatechin gallate | 75.4 ± 5.6 | 7.5 ± 1.7 |
| (−)-gallocatechin | 73.5 ± 6.7 | 3.9 ± 2.3 |
| (+)-epigallocatechin gallate | 87.5 ± 6.8 | 5.9 ± 2.0 |
| Tea extract (85% theaflavins standardized) | 100 ± 0.3 | 5.6 ± 2.1 |
| Theafalvine | 27.3 ± 1.4 | 7.9 ± 1.9 |
| Theaflavine-3'3-digallate | 100 ± 0.1 | 5.6 ± 2.3 |
| Broccoli extract | 28.6 ± 2.6 | 9.7 ± 1.8 |
| L-sulforaphane | 30.2 ± 3.6 | 6.7 ± 1.5 |
| Andrographis paniculata extract | 18.4 ± 1.8 | 5.8 ± 3.6 |
| Andrographolide | 22.1 ± 2.5 | 5.6 ± 2.4 |
| Licorice extract | 18.3 ± 3.6 | 5.7 ± 1.4 |
| Glycyrrhizic acid | 22.2 ± 2.3 | 10.1 ± 2.8 |

Figure 2:
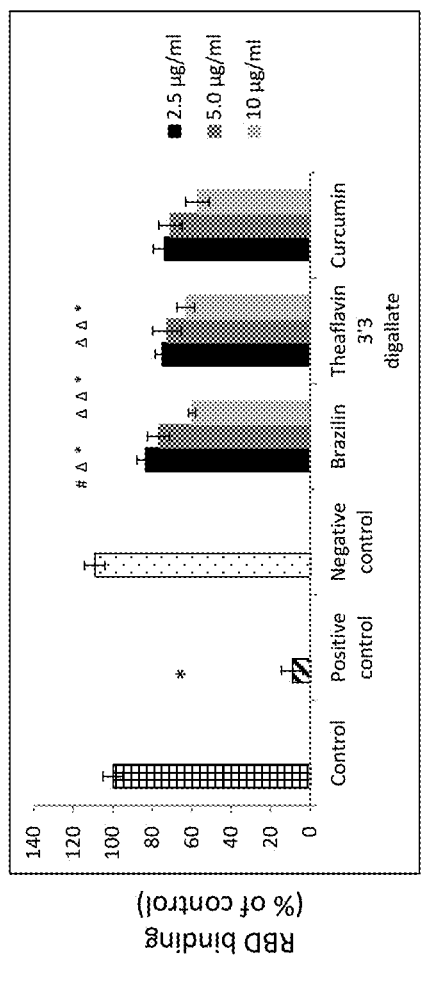
FIG. 2 shows the results of binding of the receptor binding domain (RBD) of SARS-CoV-2 to the human ACE2 receptor.

As shown in FIG. 2, the inhibitory effect of these most effective polyphenols, curcumin, theaflavin-3'3-digallate and brazilin, on RBD-hACE2 binding, was dose dependent and ranged from 20% to 95% at the concentrations from 2.5-10 μg/ml, respectively.

Figure 3:
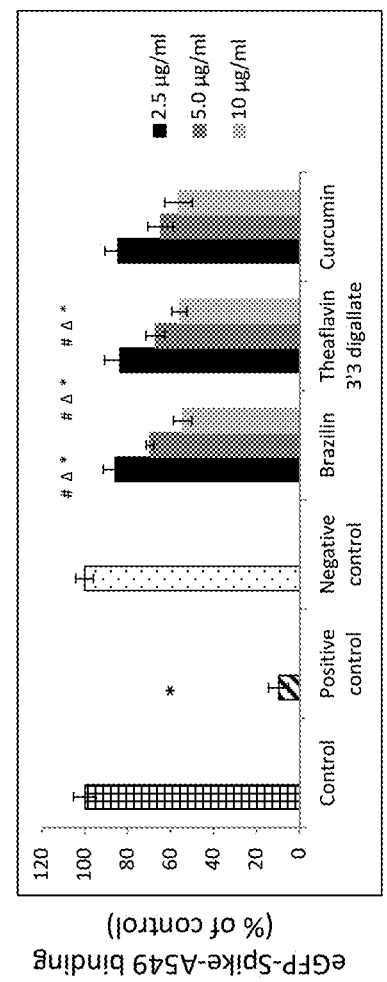
FIG. 3 shows a dose-dependent binding of SARS-CoV-2 pseudo-virions to immobilized epithelial cells overexpressing hACE2.

In a second step, we incubated A549 cells expressing SARS-CoV-2 spike protein with these three test polyphenols for 1 h. and then exposed them to soluble hACE2 receptor. In this experiment, we also observed dose-dependent interference in spike protein-hACE2 binding ranging from 15% to 95% at 2.5-10 μg/ml, respectively, which corresponded to previously obtained results (FIG. 3).

Figures 4A, 4B, 4C:
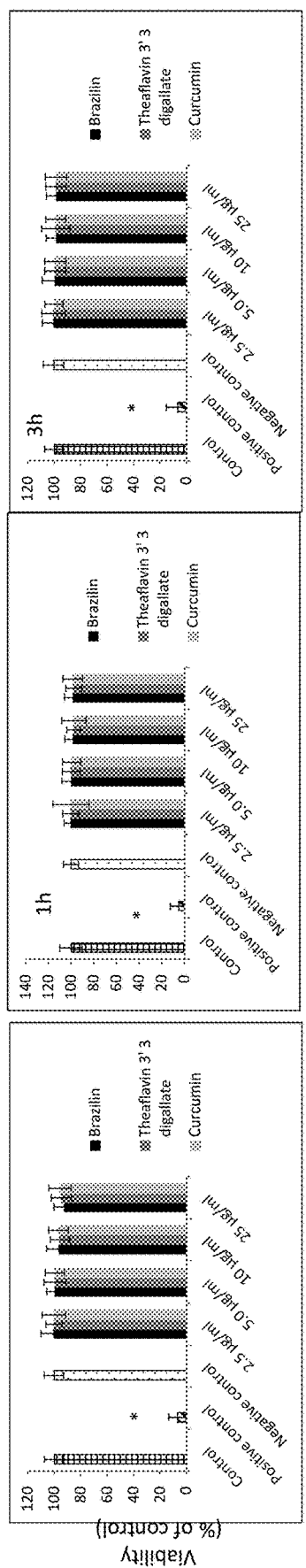
FIGS. 4A, 4B and 4C show viability of cells upon treatment with indicated polyphenols for 1 h, 3 h, and 48 h.
Figure 8:
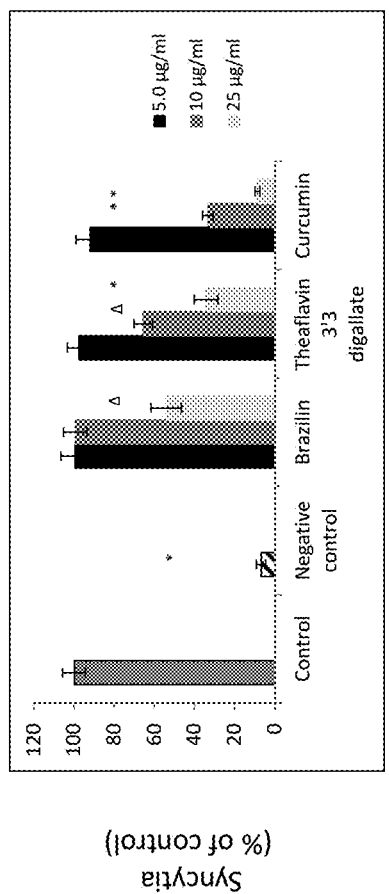
FIG. 8 shows quantification of syncytia after treatment with indicated polyphenols.

Cell viability tests revealed that short-term incubation (i.e., 1 h. and 3 h.) with these polyphenols at concentrations up to 25 μg/ml showed no cytotoxicity, as shown in FIG. 4A, FIG. 4B and FIG. 4C. As presented on FIG. 5A, brazilin, theaflavin-3,3'-digallate, and curcumin similarly inhibited binding of SARS-CoV-2 spike protein pseudo-typed virions to hACE2/A549 in dose-dependent fashion, regardless of exposure time and the application pattern. Statistically significant inhibition of pseudo-virions binding by all test polyphenols was observed already at 5.0 µg/ml and 10 µg/ml when tested before 1 h. (FIG. 5A) and simultaneously (FIG. 5B).

Another series of experiments also revealed that brazilin, theaflavin-3,3'-digallate and curcumin, applied at non-toxic concentrations (i.e., 5.0-25 µg/ml), have a similar dose-dependent inhibitory effect on binding of SARS-CoV-2 spike protein pseudo-typed virions A549 to hACE2/A549. Inhibition of virions transduction ranged from 20% to 80% without spinfection, and from 20% to 40% when spinfection was applied (FIG. 6A). Without spinfection, statistically significant inhibition by test polyphenols was observed starting from 5.0 µg/ml concentration, both when SARS-CoV-2 spike pseudo-virions were incubated with selected polyphenols 1 h. before hACE2/A549 cells exposure, and when they were added simultaneously with test polyphenols (FIG. 3A). When test polyphenols were added 1 h. after SARS-CoV-2 spike pseudo-virions were exposed to hACE2/A549 cells, significant inhibitory effect of polyphenols was observed starting from 10 µg/ml concentration.

Test polyphenols showed different efficacy on cell transduction by the pseudo-virions. When the viral transduction of hACE2/A549 cells was forced by the application of spinfection, curcumin showed significant inhibitory effect at lower concentrations compared with brazilin and theaflavin-3'3-digallate. As such, exposure of SARS-CoV-2 virions to curcumin for 1 h. before and simultaneously with adding to hACE2/A549 cells resulted in inhibition of transduction starting from its 5.0 µg/ml concentration. Higher (10 µg/ml) concentrations of brazilin and theaflavin-3,3'-digallate were required to achieve statistically significant inhibitory effects using the same patterns of exposure, All test polyphenols added 1 h. after SARS-CoV-2 virions were applied to the cells, resulted in significant inhibition of transduction at 10 µg/ml concentration of each compound (FIG. 6B).

The effect of test polyphenols on fusion of A549 cells expressing SARS-CoV-2 spike protein pseudo-typed virions with lung epithelial cells expressing hACE2 is presented in FIG. 4. A549 pseudo-virion expressing cells preincubated with test polyphenols and then layered for 4 h. on hCE2/A549 cells showed a significantly decreased attachment. Pre-incubation with brazilin at 25 µg/ml decreased cell attachment by 40%, with theaflavin-3'3-digallate by 40% to 70% at 10-25 µg/ml, and with curcumin by 70% to 95% at the same concentrations (10-25 µg/ml). These results were consistent with the previously obtained sets of data.

FIGS. 7A, 7B, 7C, 7D, 7E, 7F, 7G, 7H, 7I, 7J, 7K and FIG. 8 show the effect of test polyphenols on fusion to the human ACE2 receptor overexpressing A549 cells. A. Cell-cell fusion of A549 cells expressing eGFP spike protein with A549 cells stably expressing human ACE2 receptor. A549 cells expressing eGFP spike protein were pre-treated with indicated polyphenols at different concentrations for 1 h. at 37° C. and co-cultured for an additional 4 h. at 37° C. with A549 cells stably expressing human ACE2 receptor. The scale bar indicates 250 µm. B. Quantitative analysis of formed syncytia. Experiments were done in triplicate and repeated three times. Data are presented as percentage of control±SD; Δ p≤0.01, * p≤0.001. Control–0.025% DMSO, positive control–20 µg/ml anti-ACE2 antibody.

Figure 9:
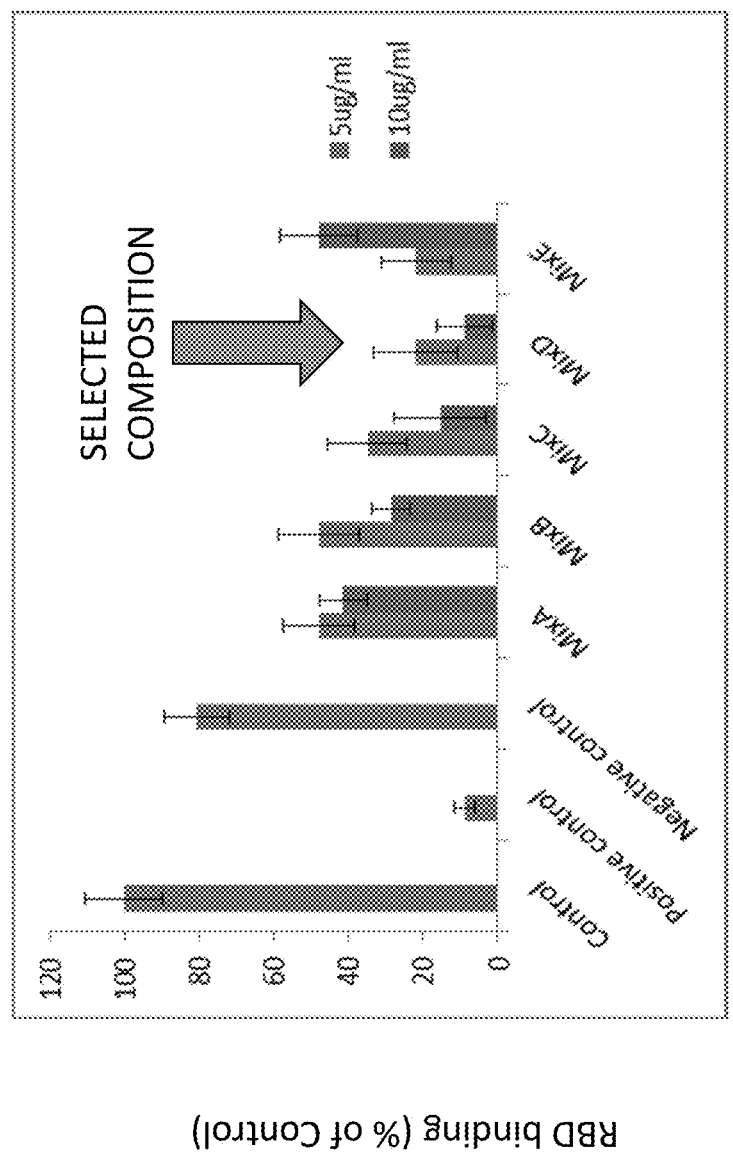
FIG. 9 shows selection of the most effective formulation based on RBD to ACE2 binding inhibition of various micronutrient mixtures.

FIG. 9 shows Mixture D (resveratrol, cruciferous plant extract, curcumin, quercetin, naringenin, baicalin, theaflavin, vitamin C and N-acetylcysteine) gives the best inhibition of binding.

Figure 10:
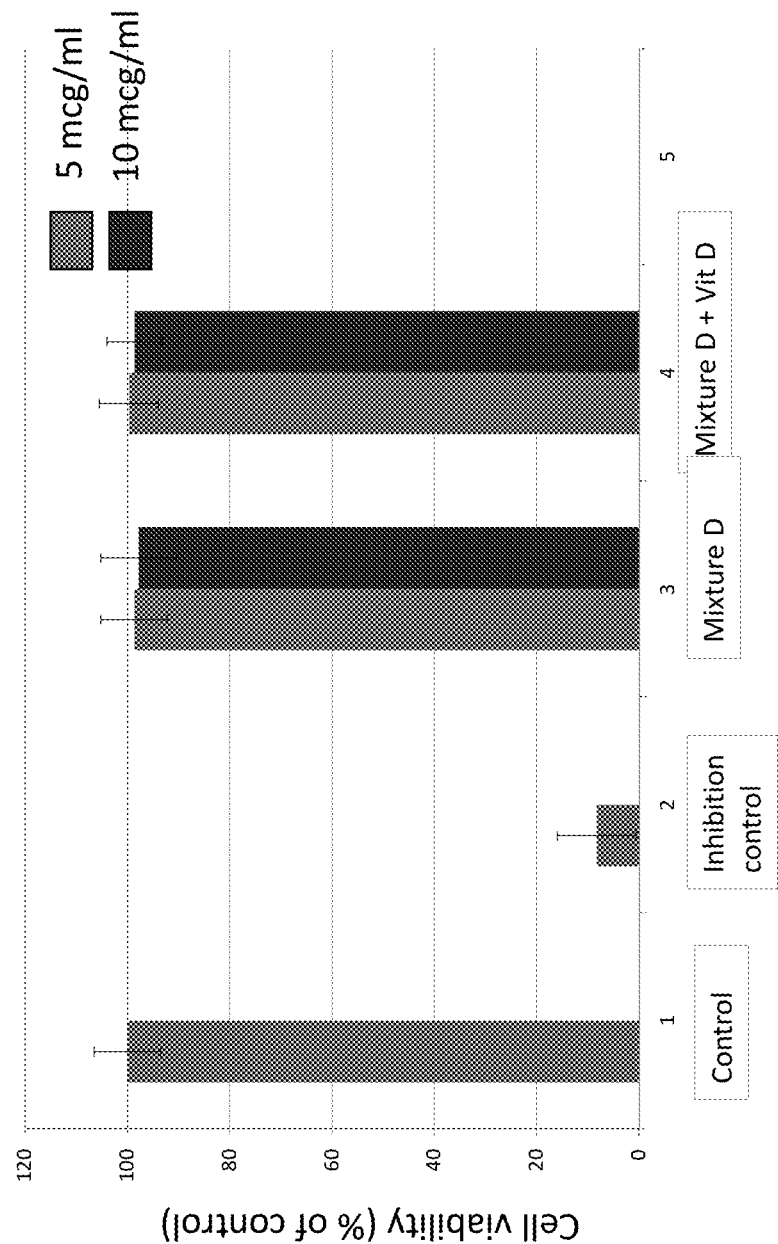
FIG. 10 shows the test for safety for mixture D in human small alveolar epithelial cells.

FIG. 10 shows the safety of the mixture D on human alveolar cells. The pharmaceutical micronutrient composition mixture D was applied at 5 and 10 mcg/ml doses individually and in combinations with vitamin D and was safe to be used on human small alveolar epithelial cells.

Figure 11:
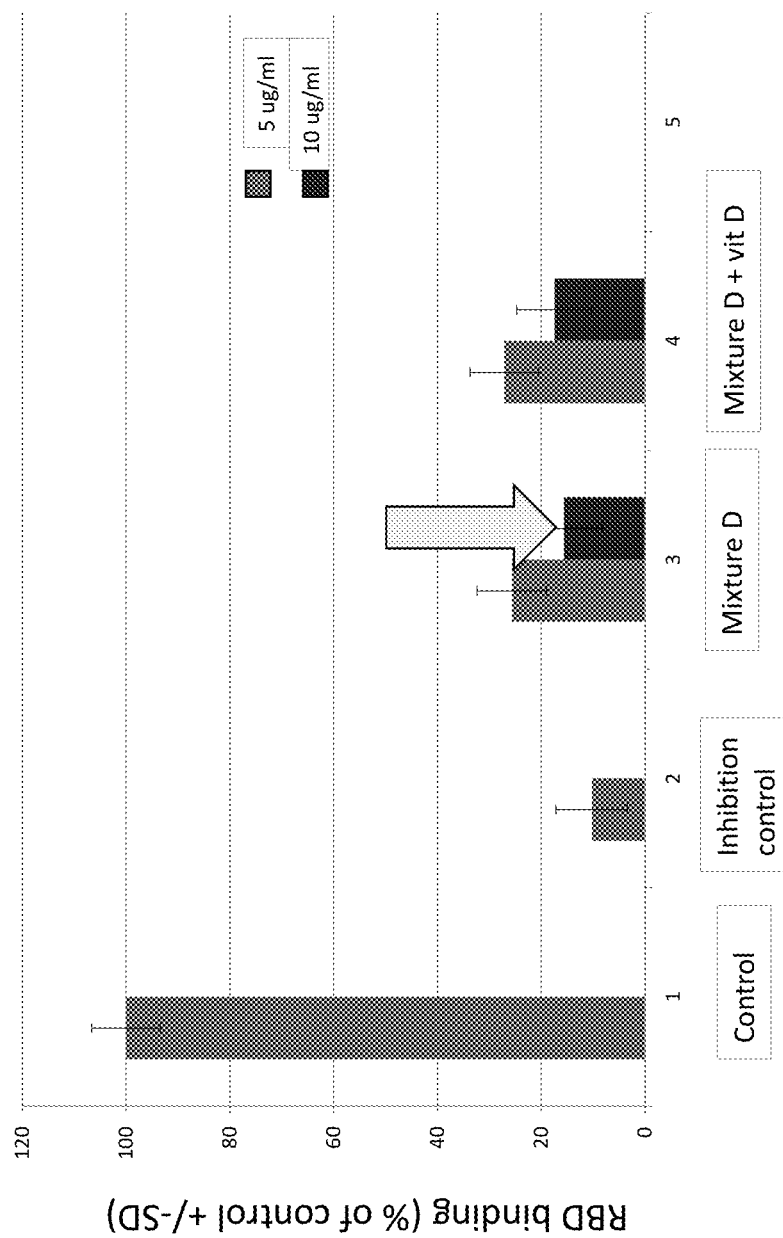
FIG. 11 shows inhibition of RBD binding and efficacy of the fMixture alone and its combination with Vitamin D.

FIG. 11 shows inhibition of RBD binding of the mixture D alone and its combination with vitamin D. Mixture D was effective in inhibiting RBD binding to ACE2 receptors by 75% at 5 mcg/ml and by 85% at 10 mcg/ml compared to control. The mixture D in combination with vitamin D did not further enhance this inhibitory effect. We can safely say that mixture D alone has high efficacy and inhibits RBD binding.

Figure 12:
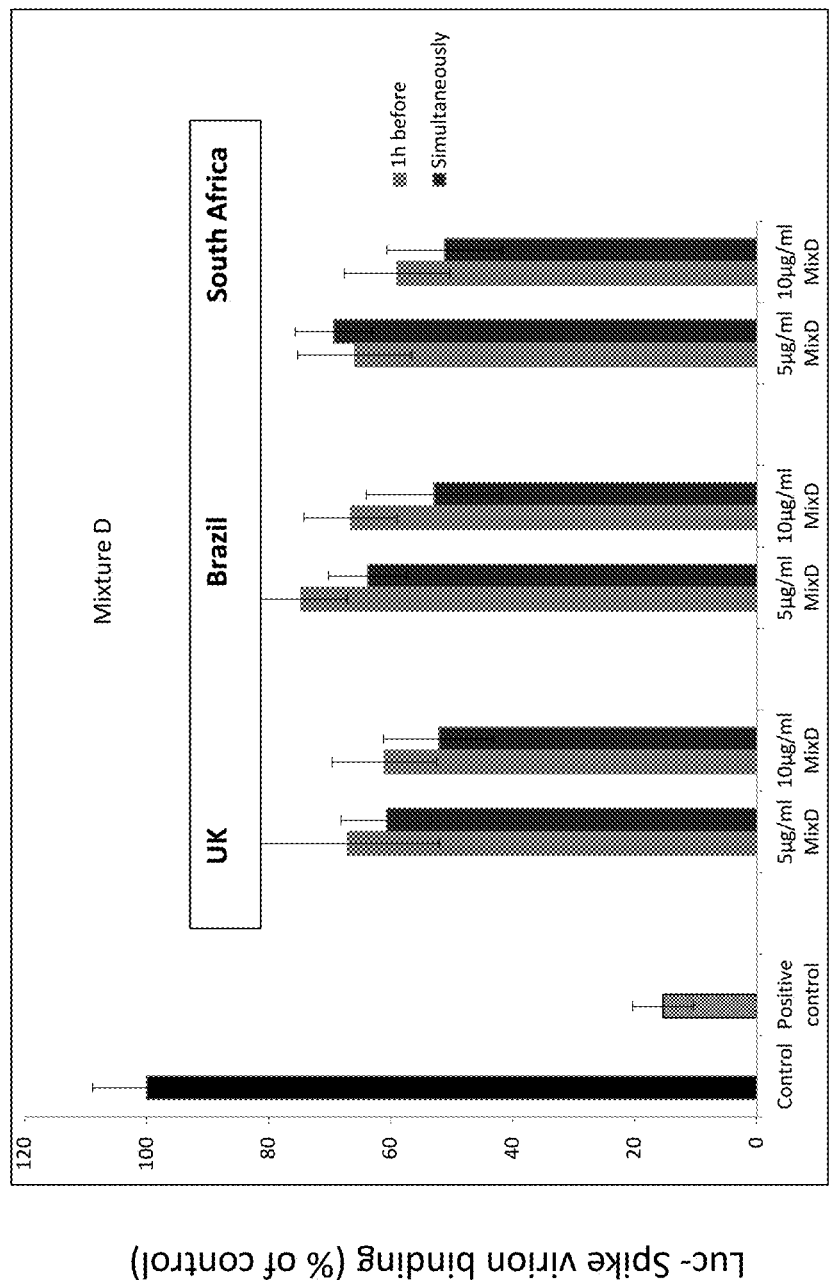
FIG. 12 shows inhibition of cellular internalization of the mutated forms of SARS-CoV-2: viral strains from the UK, Brazil, and South Africa.

FIG. 12 shows results of inhibition of cellular internalization of the mutated forms of SARS-CoV-2: viral strains from the UK, Brazil and South Africa. Mixture D (10 mcg/ml) added simultaneously with mutated virions to cells overexpressing ACE2 was equally effective in inhibiting cellular entry of these mutated forms of SARS-CoV-2: by 48% for UK mutation, by 47% for Brazilian mutation, by 48% for South African mutation. These effects were concentration dependent. Exposure of viral particles to the mixture D for 1 h, before combining them with cells also inhibited cellular entry of these viral mutants by up to 40%. These results not only show efficacy for inhibiting cellular entry by viral strains but also show that the direct exposure of viral particles to this pharmaceutical micronutrient compound helps to prevent the viral entry.

Figure 13:
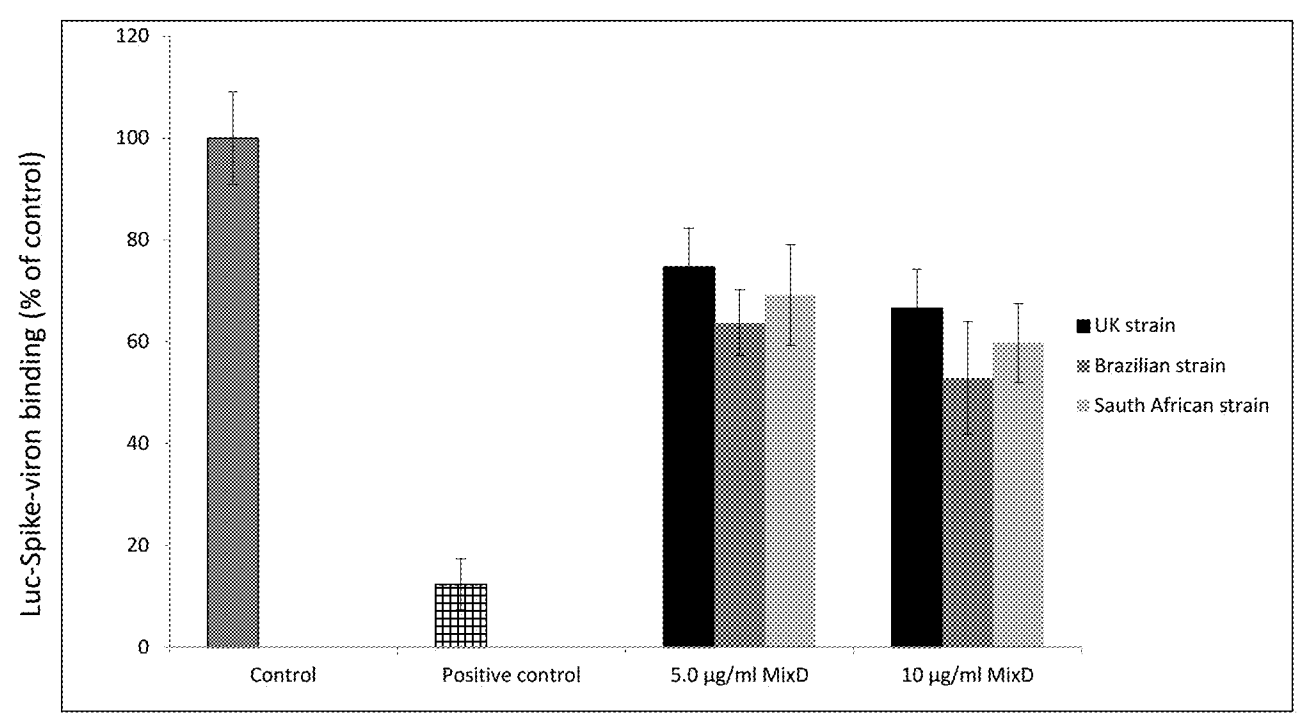

FIG. 13 shows inhibition of cellular entry by mutated forms of SARS-CoV-2, viral strains from the UK, Brazil and South Africa, owing to the inhibitory effect of the mixture D when applied simultaneously with the virions and cells.

Figure 14:
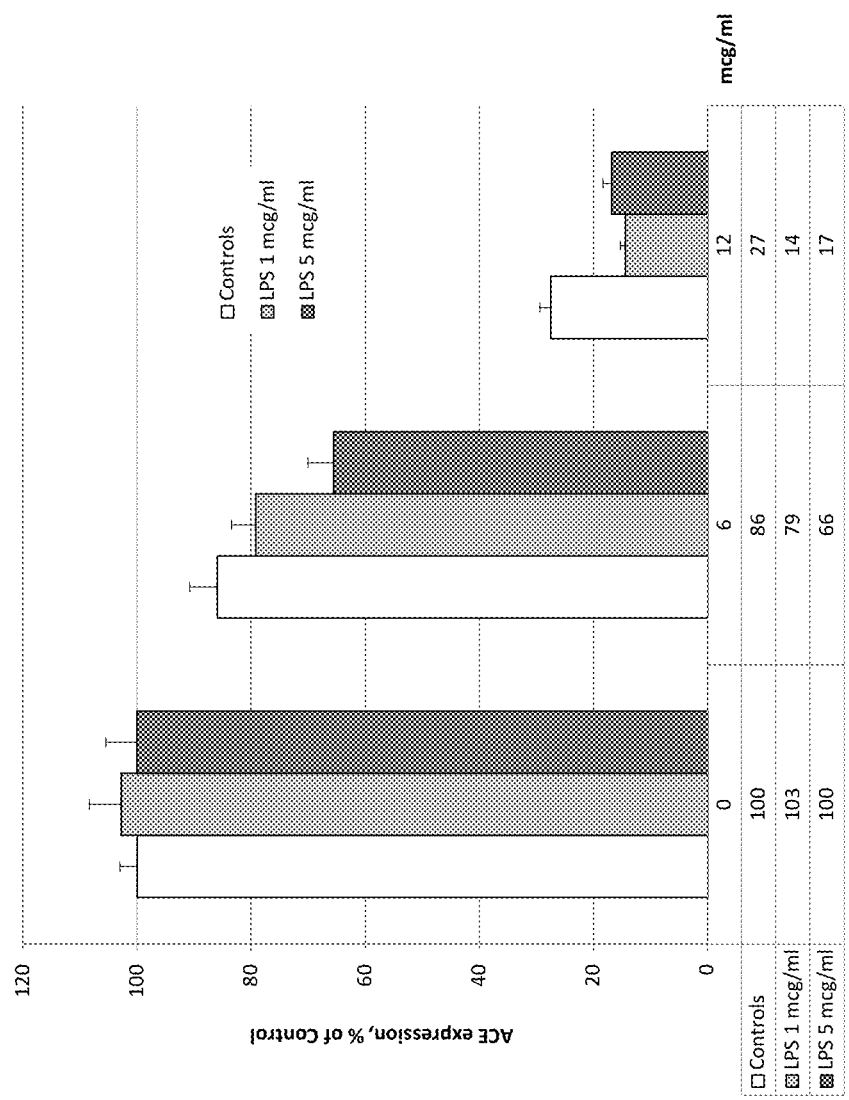
FIG. 14 shows inhibition of ACE2 expression under normal and pro-inflammatory conditions.

FIG. 14 shows inhibition of ACE2 expression under normal and pro-inflammatory conditions. Exposure of human small alveolar epithelial cells to the mixture D for 6 days resulted in inhibition of ACE2 expression by 73% at 12 mcg/ml. This inhibitory effect of the mixture D on ACE2 expression persisted and was even enhanced under pro-inflammatory conditions (inhibition between 83-86%).

Figure 15:
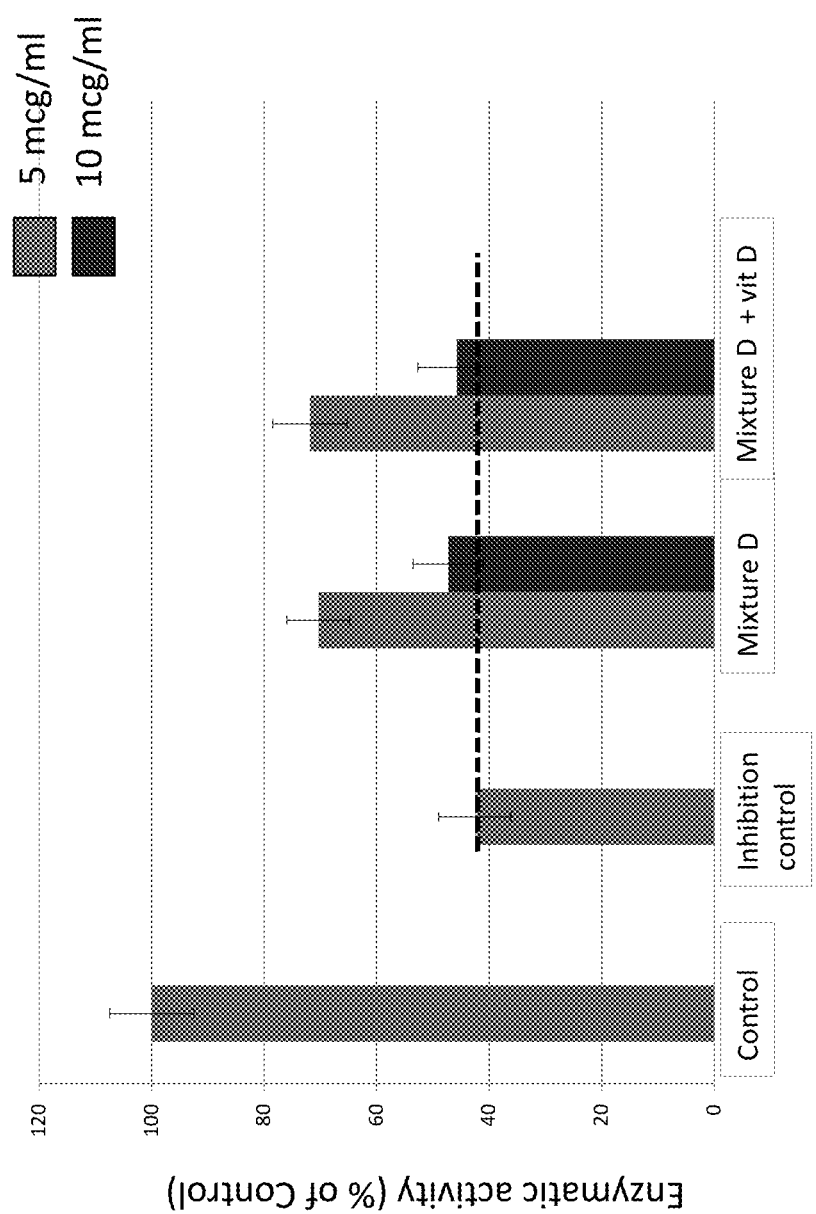
FIG. 15 shows inhibition of viral RNA-dependent RNA polymerase (RdRp) activity by mixture D with and without vitamin D.

FIG. 15 shows inhibition of viral RdRp activity and effects of vitamin D. It shows mixture D alone can inhibit RdRp activity by 53% when used at 10 mcg/ml, and by 30% at 5 mcg/ml compared to control. Combinations of the mixture D with vitamin D did not further enhance RdRp inhibition.

Figure 16:
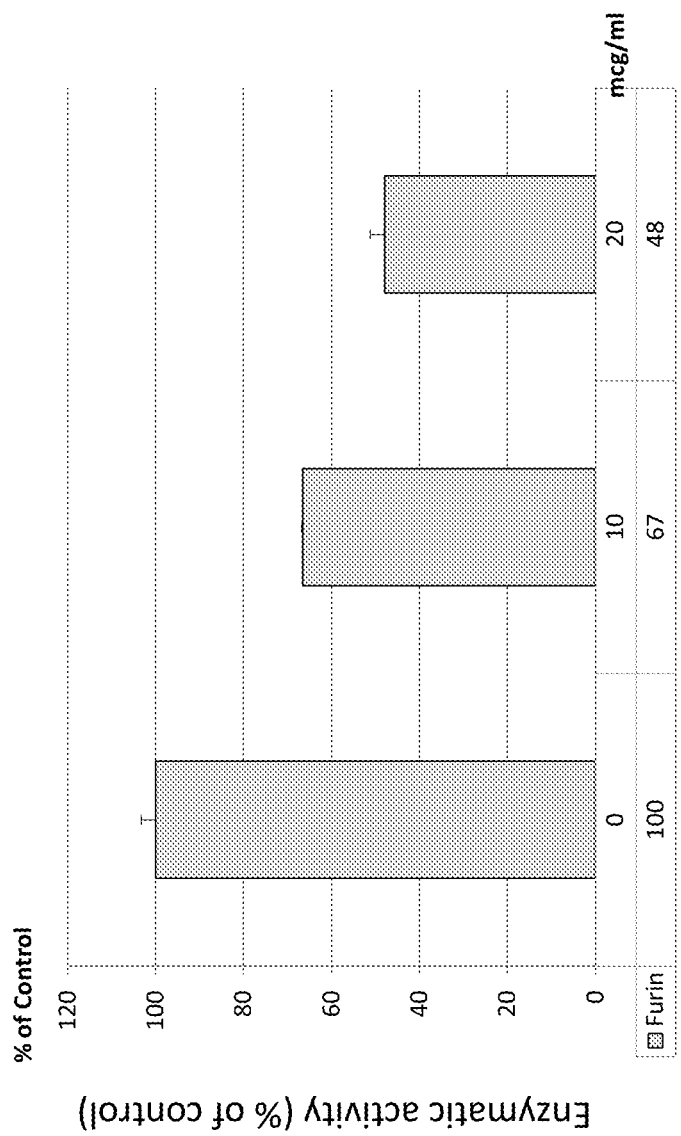
FIG. 16 shows inhibition of furin activity by mixture D.
Figure 17:
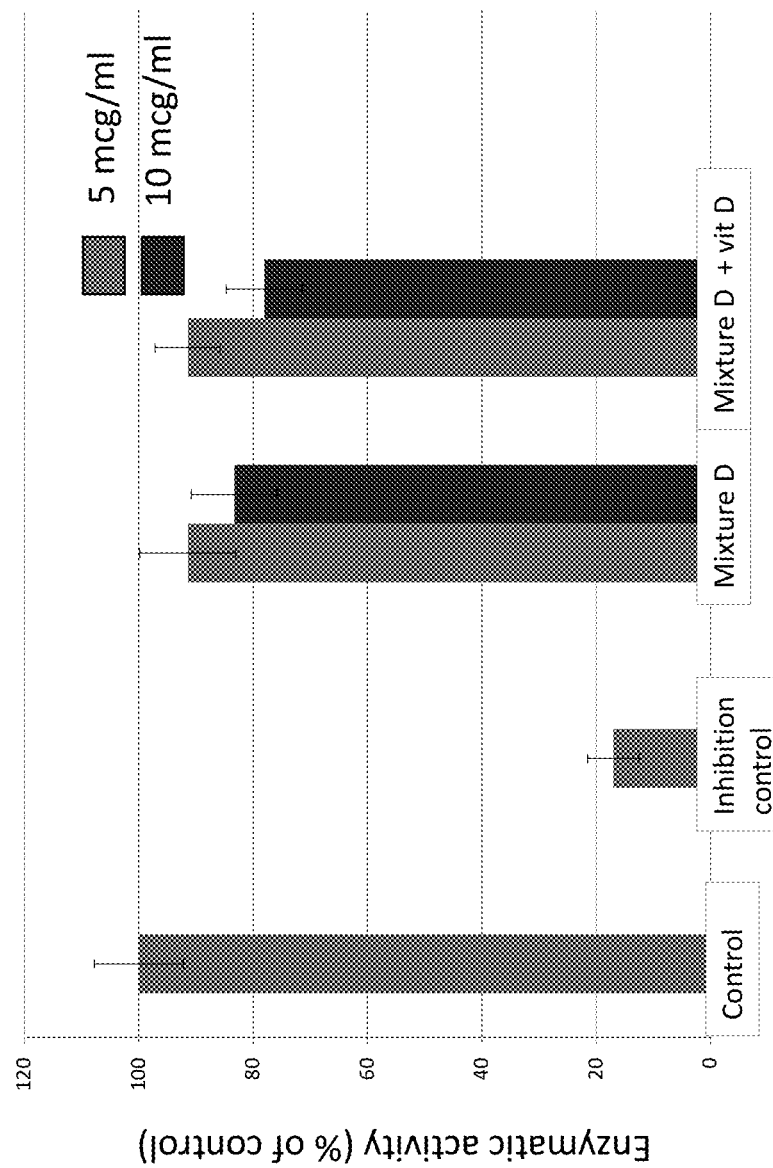
FIG. 17 shows inhibition of cellular activity of native cathepsin L by mixture D applied individually and with vitamin D.
Figure 18:
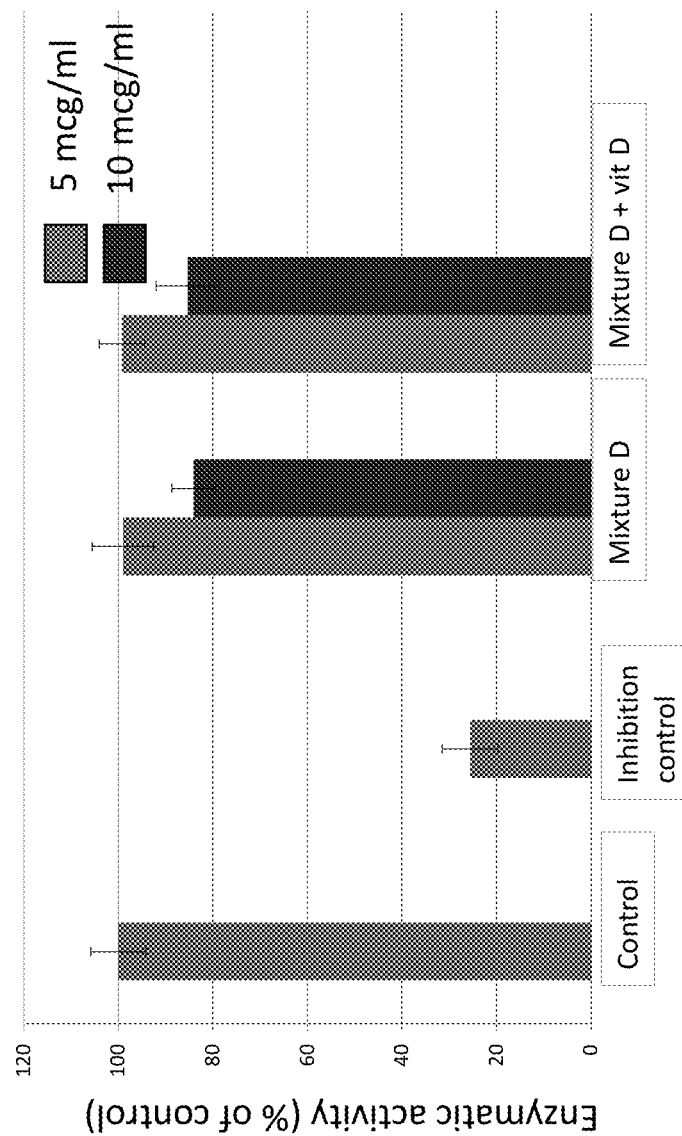
FIG. 18 shows mixture D's inhibitory effect on activity of recombinant cathepsin L and the effects of additional vitamin D.
Figure 19:
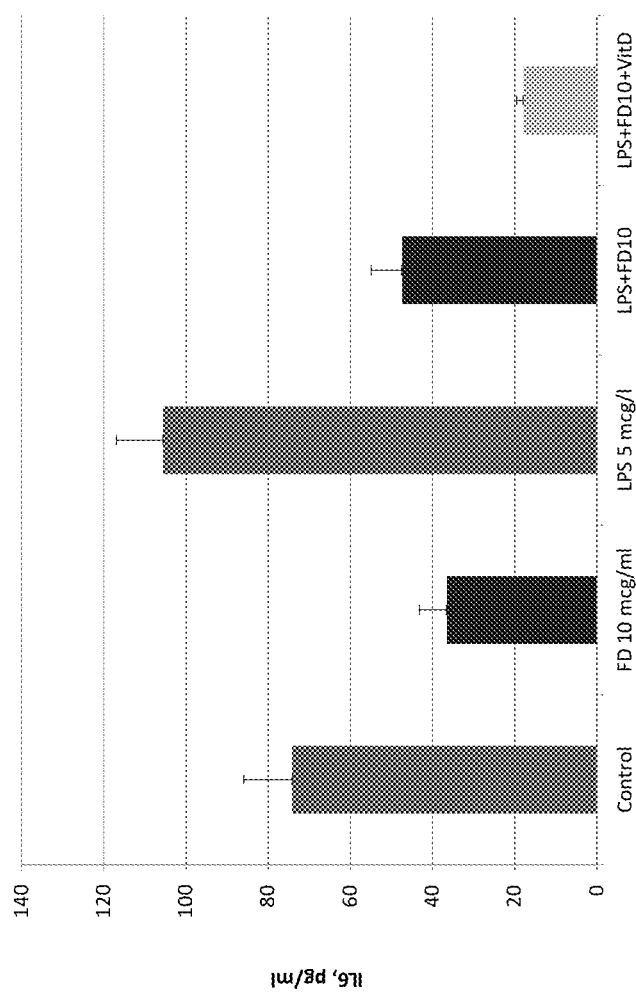
FIG. 19 shows anti-inflammatory effect: inhibition of IL6 secretion under normal and pro-inflammatory conditions by mixture D alone and combined with vitamin D.

FIG. 16 shows inhibition of furin activity in the cells, owing to mixture D activity. Mixture D applied individually at 10 mcg/ml could decrease furin activity by 33%, and at 20 mcg/ml by 52%. FIG. 17 shows the test results of inhibition of cellular activity of cathepsin L by mixture D and the effects of vitamin D and Mixture D. Mixture D applied to the cells individually and in combination with vitamin D shows 20% inhibition of cathepsin L activity. Mixture D in combination with vitamin D does not further enhance this inhibitory effect. FIG. 18 shows anti-inflammatory effect: inhibition of IL-6 secretion under normal and pro-inflammatory conditions by the mixture D alone and combined with vitamin D. Mixture D (10 mcg/ml) applied to small alveolar endothelial cells for 3 days decreased IL-6 secretion by 50%. Exposure of HSAEpC to lipopolysaccharide (LPS, 5 mcg/ml) increased IL-6 secretion by 43%. Under this pro-inflammatory condition, the mixture D could inhibit IL-6 secretion by 55%. This inhibitory effect was increased to 83% by a combination of the mixture D (10 mcg/ml) with 10 mcg/ml of vitamin D.

Drug formulations suitable for these administration routes can be produced by adding one or more pharmacologically acceptable carrier to the agent and then treating the micronutrient composition through a routine process known to those skilled in the art. The mode of administration includes, but is not limited to, non-invasive peroral, topical (for example, transdermal), enteral, transmucosal, targeted delivery, sustained-release delivery, delayed release, pulsed release and parenteral methods. Peroral administration may be administered both in liquid and dry state. In one embodiment, pharmaceutical micronutrient composition would be more specifically mixture D.

Formulations suitable for oral administration may be in the form of capsules, cachets, pills, tablets, lozenges (using a flavored bases, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin or sucrose and acacia), each containing a predetermined amount of a subject composition as an active ingredient. Subject compositions may also be administered as a bolus, electuary or paste.

When an oral solid drug product is prepared, pharmaceutical micronutrient composition is mixed with an excipient (and, if necessary, one or more additives such as a binder, a disintegrant, a lubricant, a coloring agent, a sweetening agent, and a flavoring agent), and the resultant mixture is processed through a routine method, to thereby produce an oral solid drug product such as tablets, coated tablets, granules, powder or capsules. Additives may be those generally employed in the art. Examples of excipients include lactate, sucrose, sodium chloride, glucose, starch, calcium carbonate, kaolin, microcrystalline cellulose and silicic acid. Binders include water, ethanol, propanol, simple syrup, glucose solution, starch solution, liquefied gelatin, carboxymethylcellulose, hydroxypropyl cellulose, hydroxypropyl starch, methyl cellulose, ethyl cellulose, shellac, calcium phosphate and polyvinyl pyrrolidone. Disintegrants include dried starch, sodium arginate, powdered agar, sodium hydroxy carbonate, calcium carbonate, sodium lauryl sulfate, monoglyceryl stearate and lactose. Lubricants include purified talc, stearic acid salts, borax and polyethylene glycol. Sweetening agents include sucrose, orange peel, citric acid and tartaric acid.

When a liquid drug product for oral administration is prepared, pharmaceutical micronutrient composition is mixed with an additive such as a sweetening agent, a buffer, a stabilizer, or a flavoring agent, and the resultant mixture is processed through a routine method, to produce an orally administered liquid drug product such as an internal solution medicine, syrup or elixir. Examples of the sweetening agent include vanillin; examples of the buffer include sodium citrate; and examples of the stabilizer include tragacanth, acacia, and gelatin. For the purposes of transdermal (e.g., topical) administration, dilute sterile, aqueous or partially aqueous solutions (usually in about 0.1% to 5% concentration), otherwise similar to the above parenteral solutions, may be prepared with pharmaceutical micronutrient composition.

Formulations containing pharmaceutical micronutrient composition for rectal or vaginal administration may be presented as a suppository, which may be prepared by mixing a subject composition with one or more suitable non-irritating carriers, comprising, for example, cocoa butter, polyethylene glycol, a suppository wax or a salicylate, which is solid at room temperature, but liquid at body temperature and, therefore, will melt in the appropriate body cavity and release the encapsulated compound(s) and composition(s). Formulations that are suitable for vaginal administration also include pessaries, tampons, creams, gels, pastes, foams or spray formulations containing such carriers as are known in the art to be appropriate.

A targeted-release portion for capsules containing pharmaceutical micronutrient composition can be added to the extended-release system by means of either applying an immediate-release layer on top of the extended release core; using coating or compression processes, or in a multiple-unit system such as a capsule containing extended- and immediate-release beads.

When used with respect to a pharmaceutical micronutrient composition, the term "sustained release" is art recognized. For example, a therapeutic composition that releases a substance over time may exhibit sustained-release characteristics, in contrast to a bolus type administration in which the entire amount of the substance is made biologically available at one time. In particular embodiments, upon contact with body fluids, including blood, spinal fluid, mucus secretions, lymph or the like, one or more of the pharmaceutically acceptable excipients may undergo gradual or delayed degradation (e.g., through hydrolysis), with concomitant release of any material incorporated therein, e.g., a therapeutic and/or biologically active salt and/or composition, for a sustained or extended period (as compared with the release from a bolus). This release may result in prolonged delivery of therapeutically effective amounts of any of the therapeutic agents disclosed herein.

Current efforts in the area of drug delivery include the development of targeted delivery, in which the drug is only active in the target area of the body (for example, mucous membranes such as in the nasal cavity), and sustained-release formulations, in which the pharmaceutical micronutrient composition is released over a period of time in a controlled manner from a formulation. Types of sustained release formulations include liposomes, drug-loaded biodegradable microspheres and pharmaceutical micronutrient composition polymer conjugates.

Delayed-release dosage formulations are created by coating a solid dosage form with a film of a polymer, which is insoluble in the acid environment of the stomach, but soluble in the neutral environment of the small intestine. The delayed-release dosage units can be prepared, for example, by coating a pharmaceutical micronutrient composition with a selected coating material. The pharmaceutical micronutrient composition may be a tablet for incorporation into a capsule, a tablet for use as an inner core in a "coated core" dosage form, or a plurality of drug-containing beads, particles or granules, for incorporation into either a tablet or a capsule. Preferred coating materials include bioerodible, gradually hydrolysable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract, or slowly erode as the dosage form passes through the gastrointestinal tract, while enzymatically degradable polymers are degraded by bacterial enzymes present in the lower gastrointestinal tract, particularly in the colon. Alternatively, a delayed-release tablet may be formulated by dispersing a drug within a matrix of a suitable material such as a hydrophilic polymer or a fatty compound. Suitable hydrophilic polymers include, but are not limited to, polymers or copolymers of cellulose, cellulose ester, acrylic acid, methacrylic acid, methyl acrylate, ethyl acrylate and vinyl or enzymatically degradable polymers or copolymers as described above. These hydrophilic polymers are particularly useful for providing a delayed-release matrix. Fatty compounds for use as a matrix material include, but are not limited to, waxes (e.g., carnauba wax) and glycerol tristearate. Once the active ingredient is mixed with the matrix material, the mixture can be compressed into tablets.

A pulsed-release dosage is one that mimics a multiple dosing profile without repeated dosing, and typically allows at least a twofold reduction in dosing frequency as compared with the drug presented as a conventional dosage form (e.g., as a solution or prompt drug-releasing, conventional solid dosage form). A pulsed-release profile is characterized by a time period of no release (lag time) or reduced release, followed by rapid drug release. These can be formulated for critically ill patients using the instant pharmaceutical micronutrient composition.

The phrases "parenteral administration" and "administered parenterally" as used herein refer to modes of administration other than enteral and topical, such as injections, and include without limitation intravenous, intramuscular, intrapleural, intravascular, intrapericardial, intra-arterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

Certain pharmaceutical compositions disclosed herein, suitable for parenteral administration, comprise one or more subject compositions in combination with one or more pharmaceutically acceptable sterile, isotonic, aqueous, or non-aqueous solutions, dispersions, suspensions or emulsions, or sterile powders, which may be reconstituted into sterile injectable solutions or dispersions just prior to use, and which may contain antioxidants, buffers, bacteriostats, solutes that render the formulation isotonic within the blood of the intended recipient, or suspending or thickening agents.

When an injection product is prepared, pharmaceutical micronutrient composition is mixed with an additive such as a pH regulator, a buffer, a stabilizer, an isotonicity agent or a local anesthetic, and the resultant mixture is processed through a routine method, to thereby produce an injection for subcutaneous injection, intramuscular injection, or intravenous injection. Examples of the pH regulator or buffer include sodium citrate, sodium acetate and sodium phosphate; examples of the stabilizer include sodium pyrosulfite, EDTA, thioglycolic acid, and thiolactic acid; examples of the local anesthetic include procaine hydrochloride and lidocaine hydrochloride; and examples of the isotonicity agent include sodium chloride and glucose.

Adjuvants are used to enhance the immune response. Various types of adjuvants are available. Haptens and Freund's adjuvant may also be used to produce water-in-oil emulsions of immunogens.

The phrase "pharmaceutically acceptable" is art recognized. In certain embodiments, the term includes compositions, polymers and other materials and/or dosage forms that are within the scope of sound medical judgment, suitable for use in contact with the tissues of mammals, both human beings and animals, without excessive toxicity, irritation, allergic response or other problem or complication, commensurate with a reasonable benefit-risk ratio.

The phrase "pharmaceutically acceptable carrier" is art recognized, and includes, for example, pharmaceutically acceptable materials, compositions or vehicles, such as a liquid or solid filler, diluent, solvent or encapsulating material involved in carrying or transporting any subject composition from one organ or portion of the body, to another organ or portion of the body. Each carrier must be "acceptable" in the sense of being compatible with the other ingredients of a subject composition, and not injurious to the patient. In certain embodiments, a pharmaceutically acceptable carrier is non-pyrogenic. Some examples of materials that may serve as pharmaceutically acceptable carriers include: (1) sugars, such as lactose, glucose and sucrose; (2) starches, such as corn starch and potato starch; (3) cellulose and its derivatives, such as sodium carboxymethyl cellulose, ethyl cellulose and cellulose acetate; (4) powdered tragacanth; (5) malt; (6) gelatin; (7) talc; (8) cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

In certain embodiments, the pharmaceutical micronutrient compositions described herein are formulated in a manner such that said compositions will be delivered to a mammal in a therapeutically effective amount, as part of a prophylactic, preventive or therapeutic treatment to overcome the infection caused by corona viruses (irrespective of the type).

In certain embodiments, the dosage of the pharmaceutical micronutrient compositions, which may be referred to as therapeutic composition provided herein, may be determined by reference to the plasma concentrations of the therapeutic composition or other encapsulated materials. For example, the blood samples may be tested for their immune response to their corresponding viral load or lack thereof.

The therapeutic pharmaceutical micronutrient composition provided by this application may be administered to a subject in need of treatment by a variety of conventional routes of administration, including orally, topically, parenterally, e.g., intravenously, subcutaneously or intramedullary. Further, the therapeutic compositions may be administered intranasally, as a rectal suppository, or using a "flash" formulation, i.e., allowing the medication to dissolve in the mouth without the need to use water. Furthermore, the compositions may be administered to a subject in need of treatment by controlled-release dosage forms, site-specific drug delivery, transdermal drug delivery, patch-mediated drug delivery (active/passive), by stereotactic injection, or in nanoparticles.

Expressed in terms of concentration, an active ingredient can be present in the therapeutic compositions of the present invention for localized use via the cutis, intranasally, pharyngolaryngeally, bronchially, intravaginally, rectally or ocularly.

For use as aerosols, the active ingredients can be packaged in a pressurized aerosol container together with a gaseous or liquefied propellant, for example dichlorodifluoromethane, carbon dioxide, nitrogen, propane and the like, with the usual adjuvants such as cosolvents and wetting agents, as may be necessary or desirable. The most common routes of administration also include the preferred transmucosal (nasal, buccal/sublingual, vaginal, ocular and rectal) and inhalation routes.

In addition, in certain embodiments, the subject pharmaceutical micronutrient composition of the present application may be lyophilized or subjected to another appropriate drying technique such as spray drying. The subject compositions may be administered once, or may be divided into a number of smaller doses to be administered at varying intervals of time, depending in part on the release rate of the compositions and the desired dosage.

Formulations useful in the methods provided herein include those suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of a subject pharmaceutical micronutrient composition that may be combined with a carrier material to produce a single dose may vary depending upon the subject being treated and the particular mode of administration.

The therapeutically acceptable amount described herein may be administered in inhalant or aerosol formulations. The inhalant or aerosol formulations may comprise one or more agents, such as adjuvants, diagnostic agents, imaging agents, or therapeutic agents useful in inhalation therapy. The final aerosol formulation may, for example, contain 0.005-90% w/w, for instance 0.005-50%, 0.005-5% w/w, or 0.01-1.0% w/w, of medicament relative to the total weight of the formulation.

Examples of suitable aqueous and non-aqueous carriers that may be employed in the pharmaceutical micronutrient composition include water, ethanol, polyols (such as glycerol, propylene glycol, polyethylene glycol and the like), and suitable mixtures thereof, vegetable oils such as olive oil, and injectable organic esters such as ethyl oleate. Proper fluidity may be maintained, for example by the use of coating materials such as lecithin, by the maintenance of the required particle size in the case of dispersions, and by the use of surfactants.

What is claimed is:

1. A pharmaceutical micronutrient composition, comprising:
    an ascorbate in the range of 10 mg to 200,000 mg, N-acetylcysteine in the range of 2 mg to 30,000 mg, theaflavin in the range 5 mg to 3,000 mg, resveratrol in the range of 10 mg to 5,000 mg, broccoli extract in the range of 5 mg to 5,000 mg, curcumin in the range of 5 mg to 10,000 mg, quercetin in the range of 5 mg to 2,000 mg, naringenin in the range of 5 mg to 3,000 mg, polyphenol extract from green tea in the range of 1 mg to 10,000 mg, brazilin in the range of 1 mg to 5,000 mg and baicalin in the range of 5 mg to 3,000 mg formulated as a tablet, coated tablet, capsule, pill, lozenges, emulsion, pastilles, suppository, paste and injectable solution.

2. The pharmaceutical micronutrient composition of claim 1, wherein the ascorbate is at least one of or a combination of a L-ascorbic acid, magnesium ascorbate, calcium ascorbate, ascorbyl palmitate, ascorbyl phosphate, sodium ascorbyl phosphate or another pharmaceutically acceptable form of ascorbate.

3. The pharmaceutical micronutrient composition according to claim 1, wherein the pharmaceutical micronutrient composition is effective in treating a viral infectious disease.

4. The pharmaceutical micronutrient composition according to claim 1, wherein the pharmaceutical micronutrient composition is effective in treating a viral infection in the human.

5. The pharmaceutical micronutrient composition according to claim 4, wherein the viral infection is that which uses a cellular receptor for a viral entry on a surface of an epithelial cells, endothelial cells and other cell types.

6. The pharmaceutical micronutrient composition according to claim 4, wherein the viral infection is that which uses an angiotensin converting enzyme 2 (ACE2) receptor on the surface of an epithelial cell, endothelial cell and other cell types, for the viral entry.

7. The pharmaceutical micronutrient composition according to claim 1, wherein the pharmaceutical micronutrient composition is effective in treating the human with severe acute respiratory syndrome-related coronaviruses (SARS-CoV-1), SARS-CoV2 and their variants or mutants that use angiotensin converting enzyme 2 (ACE2) receptors on the surface of epithelial cells, endothelial cells and other cell types, for viral entry.

8. The pharmaceutical micronutrient composition according to claim 1, wherein the pharmaceutical micronutrient composition is effective in treating the human and other species with a Middle East respiratory syndrome-related coronavirus (MERS-CoV), and its variants or mutants that use the angiotensin converting enzyme 2 (ACE2) receptor on the surface of epithelial cells, endothelial cells and other cell types, for viral entry.

9. The pharmaceutical micronutrient composition, wherein the pharmaceutical micronutrient composition consists of L-ascorbic acid in the range of 10 mg to 200,000 mg, N-acetylcysteine in the range of 2 mg to 30,000 mg, theaflavin in the range of 5 mg to 3,000 mg, resveratrol in the range of 10 mg to 5,000 mg, broccoli extract in the range of 5 mg to 5,000 mg, curcumin in the range of 5 mg to 10,000 mg, quercetin in the range of 5 mg to 2,000 mg, naringenin in the range of 5 mg to 3,000 mg, and baicalin in the range of 5 mg to 3,000 mg.

10. The pharmaceutical micronutrient composition according to claim 9, wherein the pharmaceutical micronutrient composition is used to treat the human and other species with a Middle East respiratory syndrome-related coronavirus (MERS-CoV), SARS CoV, SARS-CoV2 and their variants or mutants that use the angiotensin converting enzyme 2 (ACE2) receptor on the surface of epithelial cells, endothelial cells and other cell types for viral entry.

11. A pharmaceutical micronutrient composition, comprising:
    an ascorbate in the range of 10 mg to 200,000 mg, N-acetylcysteine in the range of 2 mg to 30,000 mg, theaflavin in the range 5 mg to 3,000 mg, resveratrol in the range of 10 mg to 5,000 mg, broccoli extracts in the range of 5 mg to 5,000 mg, curcumin in the range of 5 mg to 10,000 mg, quercetin in the range of 5 mg to 2,000 mg, naringenin in the range of 5 mg to 3,000 mg, and baicalin in the range of 5 mg to 3,000 mg, wherein the ascorbate is at least one of or combination of L-ascorbic acid, magnesium ascorbate, calcium ascorbate, ascorbyl palmitate, ascorbyl phosphate, sodium ascorbyl phosphate or another pharmaceutically acceptable form of ascorbate, and wherein the composition is formulated as a tablet, coated tablet, capsule, pill, lozenges, emulsion, pastilles, suppository, paste injectable solution.

12. The pharmaceutical micronutrient composition according to claim 11, wherein the pharmaceutical micronutrient composition is used to treat the human and other species with a Middle East respiratory syndrome-related coronavirus (MERS-CoV), SARS CoV, SARS-CoV2 and their variants or mutants that use the angiotensin converting enzyme 2 (ACE2) receptor on the surface of epithelial cells, endothelial cells and other cell types for viral entry.

13. The pharmaceutical micronutrient composition according to claim 11, wherein the pharmaceutical micronutrient composition is used for a treatment of a viral infection and viral disease in a human.

14. The pharmaceutical micronutrient composition according to claim 11, wherein the pharmaceutical micronutrient composition is used to treat a human with a Middle East respiratory syndrome-related coronavirus (MERS-CoV), SARS CoV, SARS-CoV2 and their variants and mutants that use the angiotensin converting enzyme 2 (ACE2) receptor on the surface of epithelial cells, endothelial cells and other cell types, for viral entry.

* * * * *